(12) United States Patent
Choon-Moon

(10) Patent No.: US 6,884,804 B2
(45) Date of Patent: Apr. 26, 2005

(54) INHIBITORS OF SRC AND OTHER PROTEIN KINASES

(75) Inventor: Young Choon-Moon, Lexington, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 33 days.

(21) Appl. No.: 10/146,984

(22) Filed: May 16, 2002

(65) Prior Publication Data

US 2003/0144309 A1 Jul. 31, 2003

Related U.S. Application Data

(60) Provisional application No. 60/291,340, filed on May 16, 2001.

(51) Int. Cl.$^7$ ..................... A61K 31/506; C07D 403/04
(52) U.S. Cl. ................. 514/275; 514/227.8; 514/235.8; 514/236.8; 514/241; 544/60; 544/122; 544/180; 544/212; 544/219; 544/238; 544/298; 544/331
(58) Field of Search ........................ 544/60, 121, 180, 544/219, 212, 238, 331, 298; 514/275, 227.8, 235.8, 241, 236.5

(56) References Cited

FOREIGN PATENT DOCUMENTS

| WO | WO 00/31063 | 6/2000 |
| WO | WO 02/22601 | 3/2002 |
| WO | WO 02/46184 | 6/2002 |

OTHER PUBLICATIONS

Zimmerman, J., et al., "Phenylamino–Pyrimidine (PAP) Derivatives: A New Class of Potent and Selective Inhibitors of Protein Kinase C (PKC)," Archiv Der Pharmazie, VCH Verlagsgesellschaft MBH, Weinheim, DE, 329(7):371–376 (1996).

*Primary Examiner*—Richard L. Raymond
(74) *Attorney, Agent, or Firm*—Nandakumar Sovindaswamy; Vertex Pharmaceuticals Incorporated

(57) ABSTRACT

The present invention provides compounds of formula I:

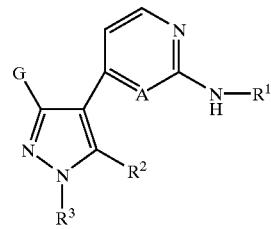

wherein A is N or CR, and G, $R^1$, $R^2$ and $R^3$ are as described in the specification. These compounds are inhibitors of protein kinase, particularly inhibitors of Src mammalian protein kinase involved in cell proliferation, cell death and response to extracellular stimuli. The invention also relates to methods for producing these inhibitors. The invention also provides pharmaceutical compositions comprising the inhibitors of the invention and methods of utilizing those compositions in the treatment and prevention of various disorders.

26 Claims, No Drawings

INHIBITORS OF SRC AND OTHER PROTEIN KINASES

CROSS REFERENCE TO RELATED APPLICATIONS

This application claims priority to U.S. Provisional Patent Application 60/291,340 filed May 16, 2001, the contents of which are incorporated herein by reference.

TECHNICAL FIELD OF INVENTION

The present invention relates to inhibitors of c-Jun N-terminal kinases (JNK) and kinases belonging to the Src family of protein kinases, especially Src and Lck protein kinases. Src family kinases are implicated in cancer, immune disorders and bone diseases. The invention also provides pharmaceutical compositions comprising the inhibitors of the invention and methods of using the compositions in the treatment of various disorders.

BACKGROUND OF THE INVENTION

Mammalian cells respond to extracellular stimuli by activating signaling cascades that are mediated by members of the mitogen-activated protein (MAP) kinase family, which include the extracellular signal regulated kinases (ERKs), the p38 MAP kinases and the c-Jun N-terminal kinases (JNKs). MAP kinases (MAPKs) are activated by a variety of signals including growth factors, cytokines, UV radiation, and stress-inducing agents. MAPKs are serine/threonine kinases and their activation occur by dual phosphorylation of threonine and tyrosine at the Thr-X-Tyr segment in the activation loop. MAPKs phosphorylate various substrates including transcription factors, which in turn regulate the expression of specific sets of genes and thus mediate a specific response to the stimulus.

One kinase family of particular interest is the Src family of kinases. These kinases are implicated in cancer, immune system dysfunction and bone remodeling diseases. For general reviews, see Thomas and Brugge, *Annu. Rev. Cell Dev. Biol.* (1997) 13, 513; Lawrence and Niu, *Pharmacol. Ther.* (1998) 77, 81; Tatosyan and Mizenina, *Biochemistry* (Moscow) (2000) 65, 49; Boschelli et al., *Drugs of the Future* 2000, 25(7), 717, (2000).

Members of the Src family include the following eight kinases in mammals: Src, Fyn, Yes, Fgr, Lyn, Hck, Lck, and Blk. These are nonreceptor protein kinases that range in molecular mass from 52 to 62 kD. All are characterized by a common structural organization that is comprised of six distinct functional domains: Src homology domain 4 (SH4), a unique domain, SH3 domain, SH2 domain, a catalytic domain (SH1), and a C-terminal regulatory region. Tatosyan et al. *Biochemistry* (Moscow) 65, 49–58 (2000).

Based on published studies, Src kinases are considered as potential therapeutic targets for various human diseases. Mice that are deficient in Src develop osteopetrosis, or bone build-up, because of depressed bone resorption by osteoclasts. This suggests that osteoporosis resulting from abnormally high bone resorption can be treated by inhibiting Src. Soriano et al., *Cell*, 69, 551 (1992) and Soriano et al., *Cell*, 64, 693 (1991).

Suppression of arthritic bone destruction has been achieved by the overexpression of CSK in rheumatoid synoviocytes and osteoclasts. Takayanagi et al., *J. Clin. Invest.*, 104, 137 (1999). CSK, or C-terminal Src kinase, phosphorylates and thereby inhibits Src catalytic activity. This implies that Src inhibition may prevent joint destruction that is characteristic in patients suffering from rheumatoid arthritis. Boschelli et al., *Drugs of the Future* 2000, 25(7), 717, (2000).

Src also plays a role in the replication of hepatitis B virus. The virally encoded transcription factor HBx activates Src in a step required for propagation of the virus. Klein et al., *EMBO J.*, 18, 5019, (1999) and Klein et al., *Mol.Cell. Biol.*, 17, 6427 (1997).

A number of studies have linked Src expression to cancers such as colon, breast, hepatic and pancreatic cancer, certain B-cell leukemias and lymphomas. Talamonti et al., *J. Clin. Invest.*, 91, 53 (1993); Lutz et al., *Biochem. Biophys. Res.* 243, 503 (1998); Rosen et al., *J. Biol. Chem.*, 261, 13754 (1986); Bolen et al., *Proc. Natl. Acad. Sci. USA*, 84, 2251 (1987); Masaki et al., *Hepatology*, 27, 1257 (1998); Biscardi et al., *Adv. Cancer Res.*, 76, 61 (1999); Lynch et al., *Leukemia*, 7, 1416 (1993); Furthermore, antisense Src expressed in ovarian and colon tumor cells has been shown to inhibit tumor growth. Wiener et al., *Clin. Cancer Res.*, 5, 2164 (1999); Staley et al., *Cell Growth Diff.*, 8, 269 (1997).

Other Src family kinases are also potential therapeutic targets. Lck plays a role in T-cell signaling. Mice that lack the Lck gene have a poor ability to develop thymocytes. The function of Lck as a positive activator of T-cell signaling suggests that Lck inhibitors may be useful for treating autoimmune disease such as rheumatoid arthritis. Molina et al., *Nature*, 357, 161 (1992). Hck, Fgr and Lyn have been identified as important mediators of integrin signaling in myeloid leukocytes. Lowell et al., *J. Leukoc. Biol.*, 65, 313 (1999). Inhibition of these kinase mediators may therefore be useful for treating inflammation. Boschelli et al., *Drugs of the Future* 2000, 25(7), 717, (2000).

In the c-Jun $NH_2$-terminal protein kinases, also known as JNKs, three distinct genes, JNK1, JNK2, JNK3 have been identified and at least ten different splicing isoforms of JNKs exist in mammalian cells [Gupta et al., *EMBO J.*, 15, 2760–70 (1996)]. Members of the JNK family are activated by proinflammatory cytokines, such as tumor necrosis factor-α (TNFα) and interleukin-1β (IL-1β), as well as by environmental stress, including anisomycin, UV irradiation, hypoxia, and osmotic shock [Minden et al., *Biochemica et Biophysica Acta*, 1333, F85–F104 (1997)].

The down-stream substrates of JNKs include transcription factors c-Jun, ATF-2, Elk1, p53 and a cell death domain protein (DENN) [Zhang et al., *Proc. Natl. Acad. Sci. USA*, 95, 2586–91 (1998)]. Each JNK isoform binds to these substrates with different affinities, suggesting a regulation of signaling pathways by substrate specificity of different JNKs in vivo (Gupta et al., supra).

JNKs, along with other MAPKs, have been implicated in the mediation of cellular response to cancer, thrombin-induced platelet aggregation, immunodeficiency disorders, autoimmune diseases, cell death, allergies, osteoporosis and heart disease. The therapeutic conditions related to activation of the JNK pathway include chronic myelogenous leukemia (CML), rheumatoid arthritis, asthma, osteoarthritis, ischemia, cancer and neurodegenerative diseases.

Several reports have detailed the importance of JNK activation associated with liver disease or episodes of hepatic ischemia [*Nat. Genet.* 21, 326–9 (1999); *FEBS Lett.* 420, 201–4 (1997); *J. Clin. Invest.* 102, 1942–50 (1998); *Hepatology* 28, 1022–30 (1998)].

A role for JNK in cardiovascular disease such as myocardial infarction or congestive heart failure has also been reported as it has been shown JNK mediates hypertrophic responses to various forms of cardiac stress [*Circ. Res.* 83, 167–78 (1998); *Circulation* 97, 1731–7 (1998); *J. Biol. Chem.* 272, 28050–6 (1997); *Circ. Res.* 79, 162–73 (1996); *Circ. Res.* 78, 947–53 (1996); *J. Clin. Invest.* 97, 508–14 (1996)].

It has been demonstrated that the JNK cascade also plays a role in T-cell activation, including activation of the IL-2 promoter. Thus, inhibitors of JNK have potential therapeutic value in altering pathologic immune responses [*J. Immunol.* 162, 3176–87 (1999); *Eur. J. Immunol.* 28, 3867–77 (1998); *J. Exp. Med.* 186, 941–53 (1997); *Eur. J. Immunol.* 26, 989–94 (1996)].

A role for JNK activation in various cancers has also been established, suggesting the potential use of JNK inhibitors in cancer. For example, constitutively activated JNK is associated with HTLV-1 mediated tumorigenesis [*Oncogene* 13, 135–42 (1996)]. The proliferative effects of bFGF and OSM on Kaposi's sarcoma (KS) cells are mediated by their activation of the JNK signaling pathway [*J. Clin. Invest.* 99, 1798–804 (1997)]. Other proliferative effects of other cytokines implicated in KS proliferation, such as vascular endothelial growth factor (VEGF), IL-6 and TNFα, are also mediated by JNK. In addition, regulation of the c-jun gene in p210 BCR-ABL transformed cells corresponds with activity of JNK, suggesting a role for JNK inhibitors in the treatment for chronic myelogenous leukemia (CML) [*Blood* 92, 2450–60 (1998)].

JNK1 and JNK2 are widely expressed in a variety of tissues. In contrast, JNK3 is selectively expressed in the brain and to a lesser extent in the heart and testis [Gupta et al., supra; Mohit et al., *Neuron* 14, 67–78 (1995); Martin et al., *Brain Res. Mol. Brain Res.* 35, 47–57 (1996)]. JNK3 has been linked to neuronal apoptosis induced by kainic acid, indicating a role of JNK in the pathogenesis of glutamate neurotoxicity. In the adult human brain, JNK3 expression is localized to a subpopulation of pyramidal neurons in the CA1, CA4 and subiculum regions of the hippocampus and layers 3 and 5 of the neocortex [Mohit et al., supra]. The CA1 neurons of patients with acute hypoxia showed strong nuclear JNK3-immunoreactivity compared to minimal, diffuse cytoplasmic staining of the hippocampal neurons from brain tissues of normal patients [Zhang et al., supra]. Thus, JNK3 appears to be involved involved in hypoxic and ischemic damage of CA1 neurons in the hippocampus.

In addition, JNK3 co-localizes immunochemically with neurons vulnerable in Alzheimer's disease [Mohit et al., supra]. Disruption of the JNK3 gene caused resistance of mice to the excitotoxic glutamate receptor agonist kainic acid, including the effects on seizure activity, AP-1 transcriptional activity and apoptosis of hippocampal neurons, indicating that the JNK3 signaling pathway is a critical component in the pathogenesis of glutamate neurotoxicity (Yang et al., *Nature*, 389, 865–870 (1997)].

Based on these findings, JNK signaling, especially that of JNK3, has been implicated in the areas of apoptosis-driven neurodegenerative diseases such as Alzheimer's Disease, Parkinson's Disease, ALS (Amyotrophic Lateral Sclerosis), epilepsy and seizures, Huntington's Disease, traumatic brain injuries, as well as ischemic and hemorrhaging stroke.

Accordingly, there is still a great need to develop potent inhibitors of JNK3, Src, and Lck protein kinases that are useful in treating various diseases or conditions associated with JNK3, Src, and Lck activation.

SUMMARY OF THE INVENTION

It has now been found that compounds of this invention, and pharmaceutically acceptable compositions thereof, are effective as inhibitors of Src, Lck, and JNK3 protein kinases. These compounds have the general formula I:

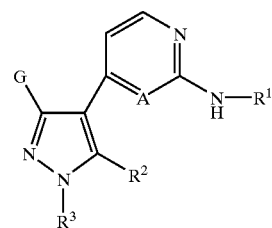

I or a pharmaceutically acceptable derivative thereof, wherein A is nitrogen or CH, and $R^1$, $R^2$, $R^3$, and G are as described below.

These compounds, and pharmaceutically acceptable compositions thereof, are useful for treating or lessening the severity of a variety of disorders, such as cancer, autoimmune disease, osteoporosis, and inflammatory diseases.

DETAILED DESCRIPTION OF THE INVENTION

The present invention relates to a compound of formula I:

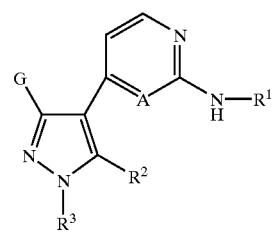

I or a pharmaceutically acceptable derivative thereof, wherein:

G is —XR or —XAr;

each X is independently selected from a $C_{1-6}$ alkylidene chain wherein one or two non-adjacent methylene units of X are independently replaced by —O—, —NR—, —S—, —C(O)—, —C(O)NR—, —NRC(O)—, —NRC(O)NR—, —SO—, —SO$_2$—, —NRSO$_2$—, —SO$_2$NR—, or —NRSO$_2$NR—;

A is N or CR;

each R is independently selected from hydrogen or an optionally substituted $C_{1-8}$ aliphatic group, or
 two R groups bound to the same nitrogen are taken together with the nitrogen to form a 3–7 membered heterocyclic ring having 0–2 heteroatoms, in addition to the nitrogen bound thereto, independently selected from nitrogen, oxygen, or sulfur; provided that when G is —N(R)$_2$, the two R groups are not taken together to form a ring;

Ar is an optionally substituted 5–6 membered saturated, partially unsaturated, or fully unsaturated monocyclic ring having zero to three heteroatoms independently selected from nitrogen, sulfur, or oxygen, or an optionally substituted 8–10 membered saturated, partially unsaturated, or fully unsaturated bicyclic ring having zero to four heteroatoms independently selected from nitrogen, sulfur, or oxygen;

$R^1$ is $T_{(n)}$—R or $T_{(n)}$—Ar;

n is zero or one;

T is selected from —C(O)—, —CO$_2$—, —C(O)C(O)—, —C(O)CH$_2$C(O)—, —CONR—, —S(O)$_2$—, or —S(O)$_2$NR—;

$R^2$ is selected from hydrogen, Ar, or a $C_{1-8}$ aliphatic group optionally substituted with 1–3 groups independently selected from oxo, OR, SR, $SO_2R$, C(O)R, $CO_2R$, CN, $N(R)_2$, =N—OR, =$NN(R)_2$, =NNHC(O)R, =$NNHCO_2R$, =$NNHSO_2R$, Ar, $NRC(O)N(R)_2$, NRC(O)R, $NRCO_2R$, $C(O)N(R)_2$, $SO_2N(R)_2$, or $NRSO_2N(R)_2$; and $R^3$ is selected from R or Ar.

As used herein, the following definitions shall apply unless otherwise indicated.

The phrase "optionally substituted" is used interchangeably with the phrase "substituted or unsubstituted." Unless otherwise indicated, an optionally substituted group may have a substituent at each substitutable position of the group, and each substitution is independent of the other.

The term "aliphatic" or "aliphatic group" as used herein means a straight-chain or branched $C_1$–$C_8$ hydrocarbon chain that is completely saturated or that contains one or more units of unsaturation, or a monocyclic $C_3$–$C_8$ hydrocarbon or bicyclic $C_8$–$C_{12}$ hydrocarbon that is completely saturated or that contains one or more units of unsaturation, but which is not aromatic (also referred to herein as "carbocycle" or "cycloalkyl"), that has a single point of attachment to the rest of the molecule wherein any individual ring in said bicyclic ring system has 3–7 members. For example, suitable aliphatic groups include, but are not limited to, linear or branched or alkyl, alkenyl, alkynyl groups and hybrids thereof such as (cycloalkyl)alkyl, (cycloalkenyl) alkyl or (cycloalkyl)alkenyl.

The terms "alkyl", "alkoxy", "hydroxyalkyl", "alkoxyalkyl", and "alkoxycarbonyl", used alone or as part of a larger moiety include both straight and branched chains containing one to twelve carbon atoms. The terms "alkenyl" and "alkynyl" used alone or as part of a larger moiety shall include both straight and branched chains containing two to twelve carbon atoms.

The term "heteroatom" means nitrogen, oxygen, or sulfur and includes any oxidized form of nitrogen and sulfur, and the quaternized form of any basic nitrogen. Also the term "nitrogen" includes a substitutable nitrogen of a heterocyclic ring. As an example, in a saturated or partially unsaturated ring having 0–3 heteroatoms selected from oxygen, sulfur or nitrogen, the nitrogen may be N (as in 3,4-dihydro-2H-pyrrolyl), NH (as in pyrrolidinyl) or $NR^+$ (as in N-substituted pyrrolidinyl).

The term "aryl" used alone or as part of a larger moiety as in "aralkyl", "aralkoxy", or "aryloxyalkyl", refers to monocyclic, bicyclic and tricyclic ring systems having a total of five to fourteen ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined hereinbelow.

The term "heterocycle", "heterocyclyl", or "heterocyclic" as used herein means non-aromatic, monocyclic, bicyclic or tricyclic ring systems having five to fourteen ring members in which one or more ring members is a heteroatom, wherein each ring in the system contains 3 to 7 ring members.

The term "heteroaryl", used alone or as part of a larger moiety as in "heteroaralkyl" or "heteroarylalkoxy", refers to monocyclic, bicyclic and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroarylalkoxy and the like) group may contain one or more substituents. Suitable substituents on the unsaturated carbon atom of an aryl, heteroaryl, aralkyl, or heteroaralkyl group are selected from halogen, —$R^°$, —$OR^°$, —$SR^°$, 1,2-methylene-dioxy, 1,2-ethylenedioxy, phenyl (Ph) optionally substituted with $R^°$, —O(Ph) optionally substituted with $R^°$, —$CH_2$(Ph) optionally substituted with $R^°$, —$CH_2CH_2$(Ph), optionally substituted with $R^°$, —$NO_2$, —CN, —$N(R^°)_2$, —$NR^°C(O)R^°$, —$NR^°C(O)N(R^°)_2$, —$NR^°CO_2R^°$, —$NR^°NR^°C(O)R^°$, —$NR^°NR^°C(O)N(R^°)_2$, —$NR^°NR^°CO_2R^°$, —$C(O)C(O)R^°$, —$C(O)CH_2C(O)R^°$, —$CO_2R^°$, —$C(O)R^°$, —$C(O)N(R^°)_2$, —$OC(O)N(R^°)_2$, —$S(O)_2R^°$, —$SO_2N(R^°)_2$, —$S(O)R^°$, —$NR^°SO_2N(R^°)_2$, —$NR^°SO_2R^°$, —C(=S)$N(R^°)_2$, —C(=NH)—$N(R^°)_2$, or —$(CH_2)_yNHC(O)R^°$, wherein each $R^°$ is independently selected from hydrogen, optionally substituted $C_{1-6}$ aliphatic, an unsubstituted 5–6 membered heteroaryl or heterocyclic ring, phenyl, —O(Ph), or —$CH_2$(Ph). Optional substituents on the aliphatic group of $R^°$ are selected from $NH_2$, NH($C_{1-4}$ aliphatic), N($C_{1-4}$ aliphatic)$_2$, halogen, $C_{1-4}$ aliphatic, OH, O($C_{1-4}$ aliphatic), $NO_2$, CN, $CO_2H$, $CO_2$($C_{1-4}$ aliphatic), O(halo $C_{1-4}$ aliphatic), or halo $C_{1-4}$ aliphatic.

An aliphatic group or a non-aromatic heterocyclic ring may contain one or more substituents. Suitable substituents on the saturated carbon of an aliphatic group or of a non-aromatic heterocyclic ring are selected from those listed above for the unsaturated carbon of an aryl or heteroaryl group and the following: =O, =S, =NNHR*, =NN(R*)$_2$, =NNHC(O)R*, =NNHCO$_2$(alkyl), =NNHSO$_2$(alkyl), or =NR*, where each R* is independently selected from hydrogen or an optionally substituted $C_{1-6}$ aliphatic. Optional substituents on the aliphatic group of R* are selected from $NH_2$, NH($C_{1-4}$ aliphatic), N($C_{1-4}$ aliphatic)$_2$, halogen, $C_{1-4}$ aliphatic, OH, O($C_{1-4}$ aliphatic), $NO_2$, CN, $CO_2H$, $CO_2$($C_{1-4}$ aliphatic), O(halo $C_{1-4}$ aliphatic), or halo ($C_{1-4}$ aliphatic).

Optional substituents on the nitrogen of a non-aromatic heterocyclic ring are selected from —$R^+$, —N($R^+$)$_2$, —C(O)$R^+$, —$CO_2R^+$, —C(O)C(O)$R^+$, —C(O)$CH_2$C(O)$R^+$, —$SO_2R^+$, —$SO_2N(R^+)_2$, —C(=S)N($R^+$)$_2$, —C(=NH)—N($R^+$)$_2$, or —$NR^+SO_2R^+$; wherein $R^+$ is hydrogen, an optionally substituted $C_{1-6}$ aliphatic, optionally substituted phenyl, optionally substituted —O(Ph), optionally substituted —$CH_2$(Ph), optionally substituted —$CH_2CH_2$(Ph), or an unsubstituted 5–6 membered heteroaryl or heterocyclic ring. Optional substituents on the aliphatic group or the phenyl ring of $R^+$ are selected from $NH_2$, NH($C_{1-4}$ aliphatic), N($C_{1-4}$ aliphatic)$_2$, halogen, $C_{1-4}$ aliphatic, OH, O($C_{1-4}$ aliphatic), $NO_2$, CN, $CO_2H$, $CO_2$($C_{1-4}$ aliphatic), O(halo $C_{1-4}$ aliphatic), or halo($C_{1-4}$ aliphatic).

The term "alkylidene chain" refers to a straight or branched carbon chain that may be fully saturated or have one or more units of unsaturation and has two points of attachment to the rest of the molecule.

A combination of substituents or variables is permissible only if such a combination results in a stable or chemically feasible compound. A stable compound or chemically feasible compound is one that is not substantially altered when kept at a temperature of 40° C. or less, in the absence of moisture or other chemically reactive conditions, for at least a week.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds that differ only in the presence of one or more isotopically enriched atoms. For example, compounds having the present structures except for the replacement of a hydrogen by a deuterium or tritium, or the replacement of a carbon by a $^{13}C$- or $^{14}C$-enriched carbon are within the scope of this invention. Such compounds are useful, for example, as analytical tools or probes in biological assays.

Preferred G groups of formula I are —X—R and —X—Ar, wherein X is a $C_{1-4}$ alkylidene chain and wherein one or two non-adjacent methylene units of X are independently replaced by —S—, —SO—, —$SO_2$—, —O—, or —NH—. More preferred X groups of formula I are selected from —S—, —O—, —NH—, —$SO_2$—, —$NHCH_2CH_2NHCH_2CH_2$—, —$NHCH_2CH_2CH_2$—, —$NHCH_2CH_2OCH_2CH_2$—, or —$NHCH_2CH_2$—.

Preferred R groups within the —X—R moiety of formula I are selected from an optionally substituted $C_{1-6}$ aliphatic group and more preferably an optionally substituted $C_{1-4}$ alkyl. Preferred substituents on the R group of —X—R of formula I are selected from halo, CN, oxo, $N(R°)_2$, OH, OR°, $CO_2R°$, C(O)R°, $C(O)N(R°)_2$, $NR°CO_2R°$, SR°, $NR°SO_2R°$, $SO_2R°$, NR°C(O)R°, OC(O)R°, or NR°C(O)N$(R°)_2$, wherein each R° group is independently selected from hydrogen or $C_{1-4}$ aliphatic. Most preferred R groups of —X—R of formula I are selected from methyl, ethyl, isopropyl, isobutyl, propyl, butyl, pentyl, hexyl, heptyl, octyl, $CH_2CN$, $CH_2OH$, $CH_2CH_2OCH_3$, $CH_2CH_2CF_3$, $CH_2$cyclopropyl, $CH_2C(O)CH_3$, $CH_2CH_2N(Me)_2$, $CH_2CH_2NHC(O)CH_3$, $CH_2CH_2NHCO_2CH_3$, $CH_2CH_2OC(O)CH_3$, $CH_2CH(NH_2)CO_2Et$, $CH_2C\equiv CCH_3$, or $CH_2CH(Me)_2$.

Preferred Ar groups within the —X—Ar moiety of formula I are selected from an optionally substituted 5–6 membered saturated or aryl ring having 0–2 heteroatoms independently selected from nitrogen, oxygen, or sulfur, or an optionally substituted 9–10 membered bicyclic aryl or heteroaryl ring having 0–2 heteroatoms independently selected from nitrogen, oxygen, or sulfur. More preferred Ar groups within —X—Ar of formula I are optionally substituted rings selected from phenyl, pyridyl, imidazolyl, thienyl, thiazolyl, [1,3]dioxanyl, piperidinyl, morpholinyl, pyrrolyl, pyrrolidinyl, furanyl, tetrahydrofuranyl, pyranyl, imidazolyl, benzimidazolyl, pyrrolyl, piperazinyl, thiomorpholinyl, naphthyl, oxazolyl, triazinyl, tetrazolyl, dithiolanyl, dioxalanyl, benzofuranyl, benzothienyl, or indolyl.

Preferred $R^1$ groups of formula I are $T_{(n)}$—Ar. Preferred Ar groups within the $R^1$ moiety are selected from an optionally substituted 6-membered saturated or aryl ring having 0–2 nitrogens, or an optionally substituted 9–10 membered partially unsaturated or fully unsaturated bicyclic ring having 0–2 heteroatoms independently selected from nitrogen, oxygen, or sulfur. More preferred Ar groups within the $R^1$ moiety are optionally substituted rings selected from phenyl, cyclohexyl, pyridyl, naphthyl, quinolinyl, isoquinolinyl, or indanyl.

Preferred substituents on Ar of $R^1$ of formula I are selected from R°, halogen, $NO_2$, CN, OR°, SR°, $N(R°)_2$, $CO_2R°$, C(O)R°, $CON(R°)_2$, phenyl, $SO_2R°$, or NR°C(O)R°, wherein each R° is independently selected from hydrogen or an optionally substituted $C_{1-4}$ aliphatic. More preferred substituents on Ar of $R^1$ of formula I are selected from methyl, ethyl, oxo, $CF_3$, OMe, C(O)Me, C(O)phenyl, $CH\equiv CH$, $CO_2H$, $C(O)NH_2$, SMe, $CO_2Me$, fluoro, $SO_2Me$, $NO_2$, CN, chloro, $N(Me)_2$, NHC(O)Me, $NH_2$, cyanophenyl, $CO_2Et$, $CH_2OH$, $CH_2OMe$, 3-$CH_2CO_2H$-phenyl, or 3-$CH_2CH_2CO_2H$-phenyl.

Preferred $R^2$ groups of formula I are selected from R, $CH_2N(R)_2$, or $CH_2Ar$, wherein R is hydrogen or optionally substituted $C_{1-4}$ aliphatic, and Ar is an optionally substituted 6 membered saturated or unsaturated ring having 0–2 heteroatoms independently selected from nitrogen, oxygen, or sulfur. More preferred $R^2$ groups of formula I are methyl, ethyl, $CH_2$(morpholin-4-yl), $CH_2N(Me)_2$, $CH_2N(Et)_2$, $CH_2N(Me)CH_2CO_2CH_3$, or $CH_2$(piperazin-1-yl).

Preferred $R^3$ groups of formula I are selected from 5–7 membered cyclic aliphatic or an optionally substituted 6 membered saturated, partially unsaturated, or fully unsaturated monocyclic ring having zero to three heteroatoms independently selected from nitrogen, sulfur, or oxygen. More preferred $R^3$ groups of formula I are selected from an optionally substituted cyclohexyl, cyclopentyl, phenyl, pyridyl, pyrimidinyl, or pyridazinyl ring.

A preferred embodiment of this invention relates to a compound of formula I where G is S—R, as shown by the general formula IA below:

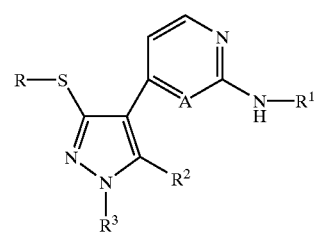

IA or a pharmaceutically acceptable derivative thereof, wherein A, R, $R^1$, $R^2$, and $R^3$ are as defined above.

Preferred R, $R^1$, $R^2$, and $R^3$ groups of formula IA are those described for formula I above.

According to a more preferred embodiment, the present invention relates to a compound of formula IIA:

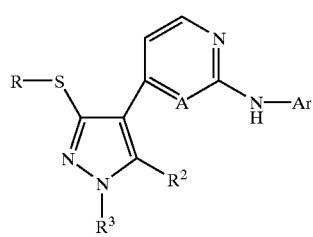

IIA or a pharmaceutically acceptable derivative thereof, wherein A, R, Ar, $R^2$, and $R^3$ are as defined above.

Preferred Ar, $R^2$, and $R^3$ groups of formula IIA are those described for formula I above.

Table 1 below shows representative examples of IIA compounds wherein A is N and Ar is an optionally substituted phenyl ring.

TABLE 1

Examples of Compounds of Formula IIA:

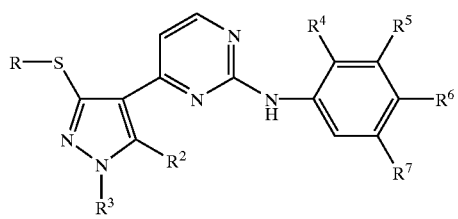

| No. | S-R | $R^2$ | $R^3$ | $R^4$ | $R^5$ | $R^6$ | $R^7$ |
|---|---|---|---|---|---|---|---|
| IIA-1 | $SCH_3$ | Me | Ph | H | H | H | H |
| IIA-2 | $SCH_3$ | Me | Ph | H | H | OMe | H |
| IIA-3 | $SCH_3$ | Me | Ph | H | OMe | OMe | H |
| IIA-4 | $SCH_3$ | Me | Ph | Me | H | H | H |
| IIA-5 | $SCH_3$ | Me | Ph | Me | H | $CONH_2$ | H |
| IIA-6 | $SCH_3$ | Me | Ph | Me | H | CN | H |
| IIA-7 | $SCH_3$ | Me | Ph | H | CN | H | H |
| IIA-8 | $SCH_3$ | Me | Ph | Me | F | H | H |
| IIA-9 | $SCH_3$ | Me | Ph | Me | H | F | H |
| IIA-10 | $SCH_3$ | Me | Ph | $CF_3$ | H | H | H |
| IIA-11 | $SCH_3$ | Et | Ph | H | CN | H | H |
| IIA-12 | $SCH_3$ | Et | Ph | H | $CO_2H$ | H | H |
| IIA-13 | $SCH_3$ | Me | Ph | H | F | H | H |
| IIA-14 | $SCH_3$ | Me | Ph | H | H | F | H |
| IIA-15 | $SCH_3$ | Me | Ph | H | H | COMe | H |
| IIA-16 | $SCH_3$ | Me | Ph | H | H | COPh | H |
| IIA-17 | $SCH_3$ | Me | Ph | H | H | $CONH_2$ | H |
| IIA-18 | $SCH_3$ | Me | Ph | H | OMe | H | OMe |
| IIA-19 | $SCH_3$ | Me | Ph | H | F | H | H |
| IIA-20 | $SCH_3$ | Me | Ph | H | H | CN | H |
| IIA-21 | $SCH_3$ | Me | Ph | H | H | COMe | H |
| IIA-22 | $SCH_3$ | Me | Ph | H | CH=CH | H | H |
| IIA-23 | $SCH_3$ | Me | Ph | H | SMe | H | H |
| IIA-24 | $SCH_3$ | Me | Ph | H | Me | CN | H |
| IIA-25 | $SCH_3$ | Me | Ph | H | COMe | H | H |
| IIA-26 | $SCH_3$ | Et | Ph | H | H | H | H |
| IIA-27 | $SCH_3$ | Me | Ph | OMe | H | H | H |
| IIA-28 | $SCH_3$ | Me | Ph | H | H | F | H |
| IIA-29 | $SCH_3$ | Me | Ph | H | $CO_2H$ | H | H |
| IIA-30 | $SCH_3$ | Me | Ph | H | H | Ph | H |
| IIA-31 | $SCH_3$ | Me | Ph | H | Me | H | Me |
| IIA-32 | $SCH_3$ | Me | Ph | H | H | SMe | H |
| IIA-33 | $SCH_3$ | Me | Ph | H | H | OMe | H |
| IIA-34 | $SCH_3$ | Me | Ph | H | OMe | H | H |
| IIA-35 | $SCH_3$ | Me | Ph | OMe | H | H | CN |
| IIA-36 | $SCH_3$ | Me | Ph | H | $CO_2Me$ | H | H |
| IIA-37 | $SCH_3$ | Me | Ph | F | H | H | CN |
| IIA-38 | $SCH_3$ | Me | Ph | H | H | H | H |
| IIA-39 | $SCH_3$ | Me | Ph | H | H | $CO_2H$ | H |
| IIA-40 | $SCH_3$ | Me | Ph | Me | H | CN | H |
| IIA-41 | $SCH_3$ | Me | Ph | F | H | F | H |
| IIA-42 | $SCH_3$ | Me | Ph | Me | H | $CONH_2$ | H |
| IIA-43 | $SCH_3$ | Me | Ph | Me | Cl | H | H |
| IIA-44 | $SCH_3$ | Me | Ph | F | H | H | H |
| IIA-45 | $SCH_3$ | Me | Ph | Me | H | OMe | H |
| IIA-46 | $SCH_3$ | Me | Ph | OMe | H | H | H |
| IIA-47 | $SCH_3$ | Me | Ph | H | H | $SO_2Me$ | H |
| IIA-48 | $SCH_3$ | Me | Ph | H | H | $CO_2Me$ | H |
| IIA-49 | $SCH_3$ | Me | Ph | $NO_2$ | H | H | H |
| IIA-50 | $SCH_3$ | Me | Ph | H | CN | H | H |
| IIA-51 | $SCH_3$ | Me | Ph | H | H | CN | H |
| IIA-52 | $SCH_3$ | Me | Ph | CHCH | H | H | H |
| IIA-53 | $SCH_3$ | Me | Ph | Me | F | H | H |
| IIA-54 | $SCH_3$ | Me | Ph | Cl | H | H | OMe |
| IIA-55 | $SCH_3$ | Me | Ph | H | Me | OMe | H |
| IIA-56 | $SCH_3$ | Me | Ph | Me | H | F | H |
| IIA-57 | $SCH_3$ | Me | Ph | SMe | H | H | H |
| IIA-58 | $SCH_3$ | Me | Ph | OMe | H | H | OMe |
| IIA-59 | $SCH_2CH_3$ | Me | Ph | H | H | H | H |
| IIA-60 | $SCH_2CH_3$ | Me | Ph | H | CN | H | H |
| IIA-61 | $SCH_2CH_3$ | Me | Ph | H | H | CN | H |
| IIA-62 | $SCH_2CH_3$ | Me | Ph | H | F | H | H |
| IIA-63 | $SCH_2CH_3$ | Me | Ph | H | H | F | H |
| IIA-64 | $SCH_2CH_3$ | Me | Ph | H | Me | CN | H |

TABLE 1-continued

Examples of Compounds of Formula IIA:

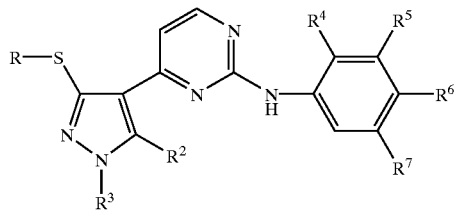

| No. | S-R | $R^2$ | $R^3$ | $R^4$ | $R^5$ | $R^6$ | $R^7$ |
|---|---|---|---|---|---|---|---|
| IIA-65 | $SCH_2CH_3$ | Me | Ph | H | F | CN | H |
| IIA-66 | $SCH_2CH_3$ | Me | Ph | H | H | SMe | H |
| IIA-67 | $SCH(CH_3)_2$ | Me | Ph | H | H | H | H |
| IIA-68 | $SCH_2CH(CH_3)_2$ | Me | Ph | H | H | H | H |
| IIA-69 | S-propyl | Me | Ph | H | H | H | H |
| IIA-70 | S-butyl | Me | Ph | H | H | H | H |
| IIA-71 | S-pentyl | Me | Ph | H | H | H | H |
| IIA-72 | S-hexyl | Me | Ph | H | H | H | H |
| IIA-73 | S-heptyl | Me | Ph | H | H | H | H |
| IIA-74 | S-octyl | Me | Ph | H | H | H | H |
| IIA-75 | $SCH_2CN$ | Me | Ph | H | H | H | H |
| IIA-76 | $SCH_2CH_2OCH_3$ | Me | Ph | H | H | H | H |
| IIA-77 | $SCH_2CH_2CF_3$ | Me | Ph | H | H | H | H |
| IIA-78 | $SCH_2$(cyclopropyl) | Me | Ph | H | H | H | H |
| IIA-79 | $SCH_2C(=O)CH_3$ | Me | Ph | H | H | H | H |
| IIA-80 | $SCH_2CH_2N(CH_3)_2$ | Me | Ph | H | H | H | H |
| IIA-81 | $SCH_2CH_2NHCOCH_3$ | Me | Ph | H | H | H | H |
| IIA-82 | $SCH_2CH_2NHCO_2CH_3$ | Me | Ph | H | H | H | H |
| IIA-83 | $SCH_2CH_2OC(=O)CH_3$ | Me | Ph | H | H | H | H |
| IIA-84 | $SCH_2CH(NH_2)CO_2Et$ | Me | Ph | H | H | H | H |
| IIA-85 | $SCH_2C\equiv CCH_3$ | Me | Ph | H | H | H | H |
| IIA-86 | S-propyl | Me | Ph | H | H | COMe | H |
| IIA-87 | S-propyl | Me | Ph | H | CN | H | H |
| IIA-88 | S-propyl | Me | Ph | H | H | CN | H |
| IIA-89 | S-propyl | Me | Ph | H | F | H | H |
| IIA-90 | S-propyl | Me | Ph | H | H | F | H |
| IIA-91 | S-propyl | Me | Ph | H | CN | F | H |
| IIA-92 | S-propyl | Me | Ph | H | H | SMe | H |
| IIA-93 | $SCH_3$ | Me | Ph | H | H | $NMe_2$ | H |
| IIA-94 | $SCH_3$ | Me | Ph | H | $NO_2$ | H | H |
| IIA-95 | $SCH_3$ | Me | Ph | H | NHAc | H | H |
| IIA-96 | $SCH_3$ | Me | Ph | H | $NH_2$ | H | H |
| IIA-97 | $SCH_3$ | Me | Ph | H | Me | H | H |
| IIA-98 | $SCH_3$ | Me | Ph | H | H | Me | H |
| IIA-99 | S-butyl | Me | Ph | H | F | CN | H |
| IIA-100 | S-butyl | Me | Ph | H | F | H | H |
| IIA-101 | S-butyl | Me | Ph | H | H | CN | H |
| IIA-102 | S-butyl | Me | Ph | H | Me | H | H |
| IIA-103 | S-butyl | Me | Ph | H | CN | H | H |
| IIA-105 | S-pentyl | Me | Ph | H | F | CN | H |
| IIA-106 | S-pentyl | Me | Ph | H | CN | H | H |
| IIA-107 | $SCH_2CH(CH_3)_2$ | Me | Ph | H | F | CN | H |
| IIA-108 | $SCH_2CH(CH_3)_2$ | Me | Ph | H | CN | H | H |
| IIA-109 | $SCH_2CH(CH_3)_2$ | Me | Ph | bis-N,N'-4-cyanophenyl | | | |

TABLE 1-continued

Examples of Compounds of Formula IIA:

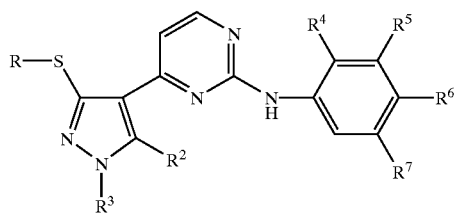

| No. | S-R | R² | R³ | R⁴ | R⁵ | R⁶ | R⁷ |
| --- | --- | --- | --- | --- | --- | --- | --- |
| IIA-110 | SCH$_2$C≡CCH$_3$ | Me | Ph | H | F | CN | H |
| IIA-111 | SCH$_2$C≡CCH$_3$ | Me | Ph | H | CN | H | H |
| IIA-112 | SCH$_2$C≡CCH$_3$ | Me | Ph | H | H | H | H |
| IIA-113 | SCH$_3$ | Me | Ph | H | CO$_2$Et | H | H |
| IIA-114 | SCH$_3$ | Me | Ph | H | H | Cl | H |
| IIA-115 | SCH$_3$ | Me | Ph | H | Cl | H | H |
| IIA-116 | SCH$_3$ | Me | Ph | H | H | NO$_2$ | H |
| IIA-117 | SCH$_3$ | Me | Ph | H | OCH$_2$Ph | H | H |
| IIA-118 | SCH$_3$ | Me | Ph | H | H | OCH$_2$Ph | H |
| IIA-119 | SCH$_3$ | Me | Ph | H | OH | H | H |
| IIA-120 | SCH$_3$ | Me | Ph | | (3-substituted phenyl with CH$_2$CH$_2$CO$_2$H) | | |
| IIA-121 | SCH$_3$ | Me | Ph | | (3-substituted phenyl with CH$_2$CO$_2$H) | | |
| IIA-122 | SCH$_3$ | Me | Ph | | (3-substituted phenyl with CH$_2$CH$_2$C(O)NH-CH(iPr)-CO$_2$$^t$Bu) | | |
| IIA-123 | SCH$_3$ | Me | 2-Pyr | H | H | H | H |
| IIA-124 | SCH$_3$ | Me | 2-Pyr | H | OCH$_2$Ph | H | H |
| IIA-125 | SCH$_3$ | Me | 3-Pyr | H | OCH$_2$Ph | H | H |
| IIA-126 | SCH$_3$ | Me | 4-Pyr | H | OCH$_2$Ph | H | H |
| IIA-127 | SCH$_3$ | Me | Ph | H | Cl | H | H |
| IIA-128 | SCH$_3$ | Me | 2-Pyr | H | H | OCH$_2$Ph | H |
| IIA-129 | CH$_2$CH$_2$SCH$_3$ | Me | Ph | H | OCH$_2$Ph | H | H |
| IIA-130 | CH$_2$CH$_2$SCH$_3$ | Me | Ph | H | OPh | H | H |
| IIA-131 | CH$_2$CH$_2$SCH$_3$ | Me | Ph | H | Cl | H | H |
| IIA-132 | CH$_2$CH$_2$SCH$_3$ | Me | Ph | H | OMe | H | H |
| IIA-133 | CH$_2$CH$_2$SCH$_3$ | Me | Ph | H | CO$_2$CH$_3$ | H | H |
| IIA-134 | SCH$_3$ | Me | Ph | H | OH | H | H |

Examples of compounds of Formula IIA where R² is methyl, R³ is phenyl, and R¹ is other than phenyl are shown below in Table 2.

TABLE 2

Examples of Compounds of Formula IIA

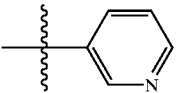

| No. | S-R | A | R¹ |
|---|---|---|---|
| IIA-135 | SCH₃ | CH | 3-pyridyl |
| IIA-136 | SCH₃ | CH | 6-methoxy-3-pyridyl |
| IIA-137 | SCH₃ | N | 4-methyl-1-naphthyl |
| IIA-138 | SCH₃ | N | 2-naphthyl |
| IIA-139 | SCH₃ | N | 3-pyridyl |
| IIA-140 | SCH₃ | N | 4-isoquinolinyl |
| IIA-141 | SCH₃ | N | 8-quinolinyl |

TABLE 2-continued

Examples of Compounds of Formula IIA

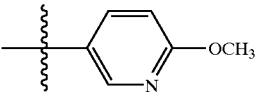

| No. | S-R | A | R¹ |
|---|---|---|---|
| IIA-142 | SCH₃ | N | 2-methyl-6-quinolinyl |
| IIA-143 | SCH₃ | N | 7-methoxy-2-naphthyl |
| IIA-144 | SCH₃ | N | 6-methoxy-2-naphthyl |
| IIA-145 | SCH₃ | N | 1-oxo-indanyl |
| IIA-146 | SCH₃ | N | 4-methyl-2-pyridyl |
| IIA-147 | SCH₃ | N | 1-naphthyl |

TABLE 2-continued

Examples of Compounds of Formula IIA

| No. | S-R | A | R¹ |
|---|---|---|---|
| IIA-148 | S-propyl | N | 6-(2-methoxynaphthalen-6-yl) |
| IIA-149 | SCH₃ | N | 1-(2-methylnaphthalen-1-yl) |
| IIA-150 | SCH₃ | N | 6-(2-(CO₂Me)naphthalen-6-yl) |
| IIA-151 | SCH₃ | N | 1-(2-methoxynaphthalen-1-yl) |
| IIA-152 | SCH₃ | N | 1-(2-(OMe-CH₂)naphthalen-1-yl) |
| IIA-153 | S-butyl | N | 6-(2-methoxynaphthalen-6-yl) |
| IIA-154 | S-butyl | N | 6-(2-methylquinolin-6-yl) |
| IIA-155 | S—CH₂CN | N | 6-(2-methylquinolin-6-yl) |

Representative examples of compounds of formula IIA wherein A is CH, G is S—Me, R¹ is phenyl, R³ is phenyl, and R² is other than methyl are shown in Table 3 below.

TABLE 3

Examples of Compound IIA

| No. | R² |
|---|---|
| IIA-156 | CH₂(morpholin-4-yl) |
| IIA-157 | CH₂N(CH₃)₂ |
| IIA-158 | CH₂NEt₂ |
| IIA-159 | CH₂N(CH₃)CH₂Ph |
| IIA-160 | CH₂N(CH₃)CH₂CO₂CH₃ |
| IIA-161 | CH₂(piperazin-1-yl) |

Another embodiment of this invention relates to a compound of formula IB or IB':

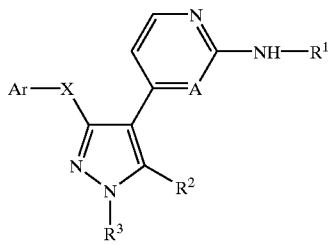

IB

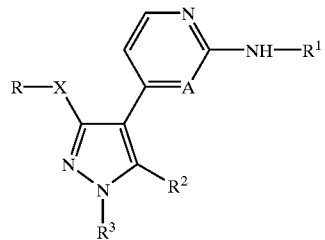

IB' or a pharmaceutically acceptable derivative thereof, wherein each X is independently selected from a $C_{1-4}$ alkylidene chain and wherein one or two non-adjacent methylene units of X are independently replaced by —S—, —SO$_2$—, —O—, or —NH—, and wherein A, R, Ar, R$^1$, R$^2$, and R$^3$ are as defined above.

Preferred R, Ar, R$^1$, R$^2$, and R$^3$ groups within formulae IB and IB' are as described above for formula I.

Table 4 below shows specific examples of formula IB and IB' compounds.

TABLE 4

Examples of IB Compounds

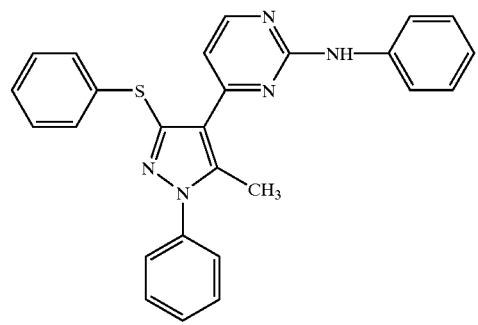

IB-1

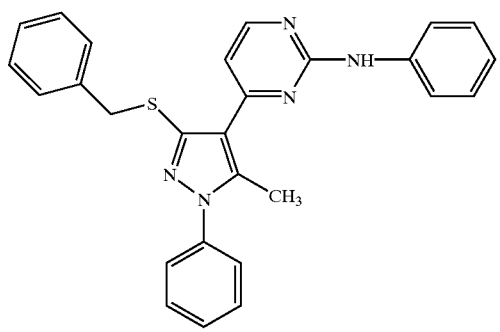

IB-2

TABLE 4-continued

Examples of IB Compounds

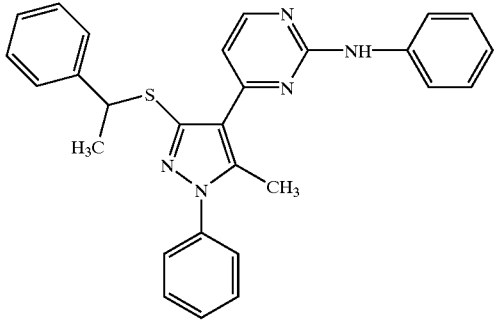

IB-3

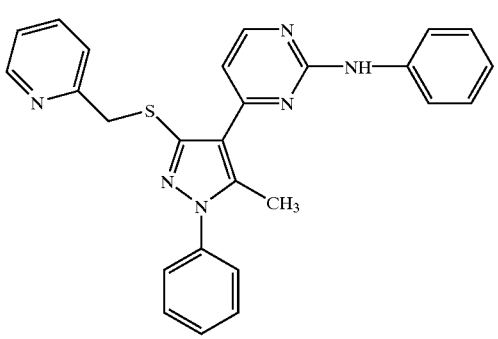

IB-4

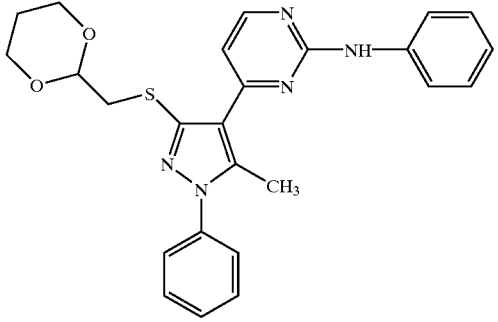

IB-5

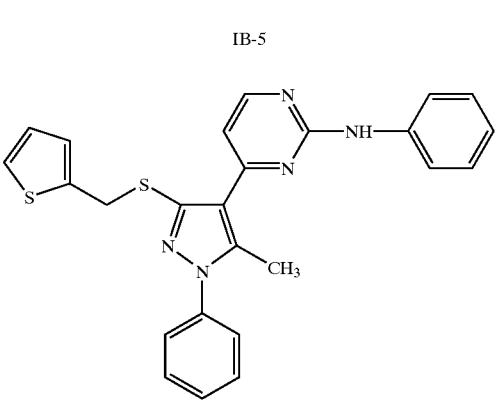

IB-6

TABLE 4-continued
Examples of IB Compounds
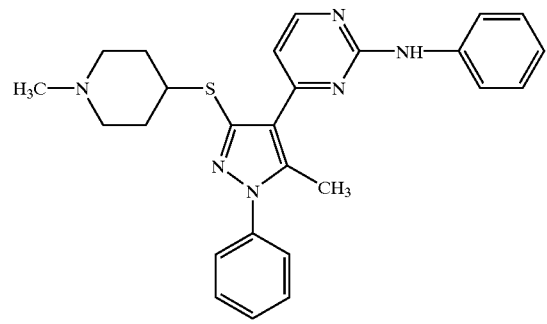
IB-7
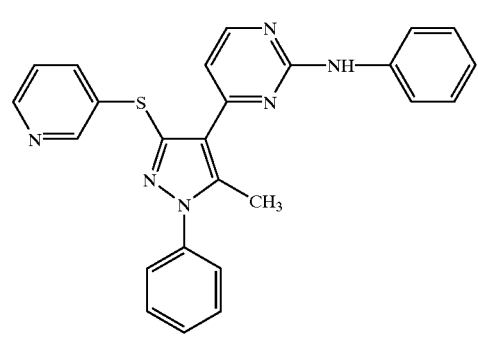
IB-8
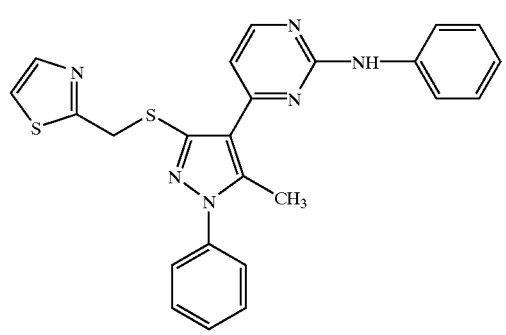
IB-9
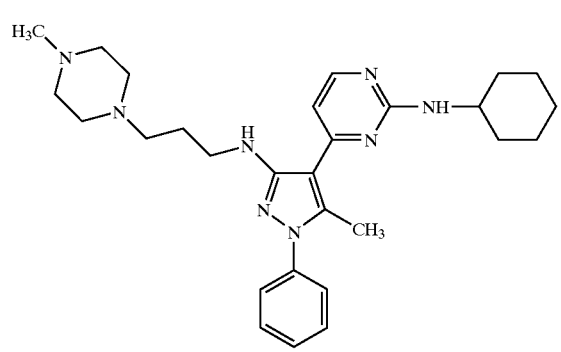
IB-10
TABLE 4-continued
Examples of IB Compounds
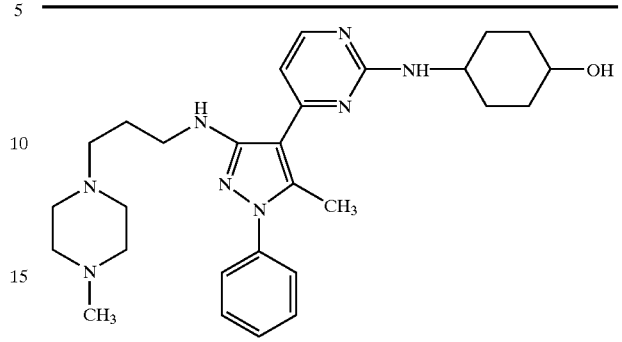
IB-11
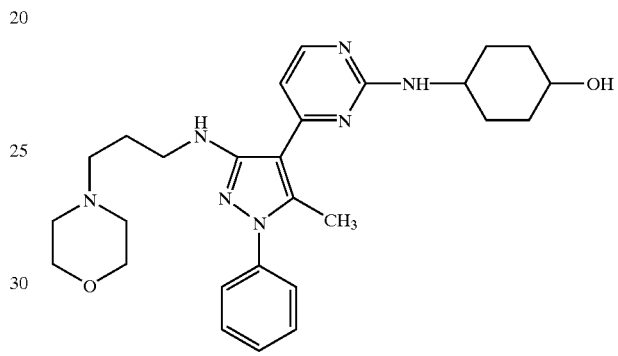
IB-12
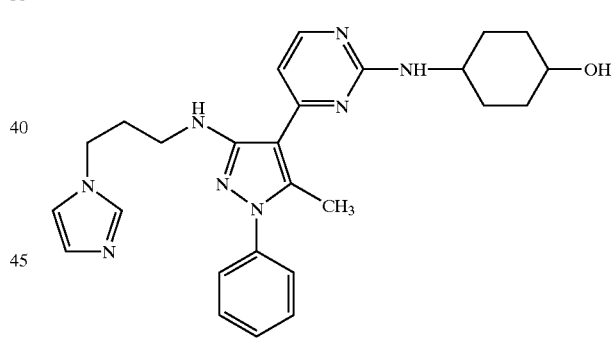
IB-13
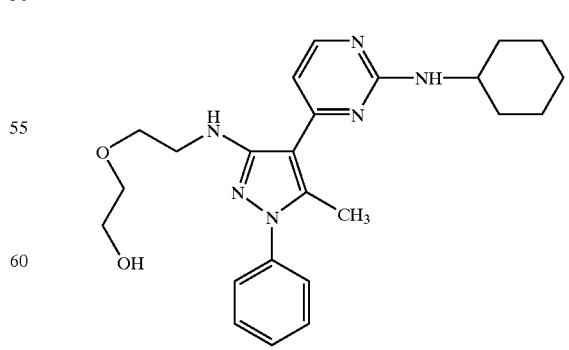
IB'-1

TABLE 4-continued

Examples of IB Compounds

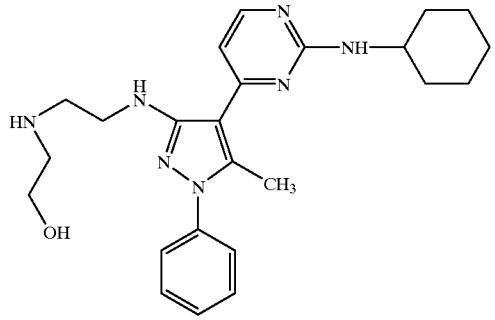

IB'-2

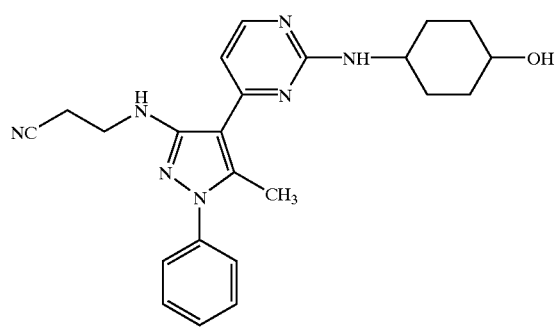

IB'-3

TABLE 4-continued

Examples of IB Compounds

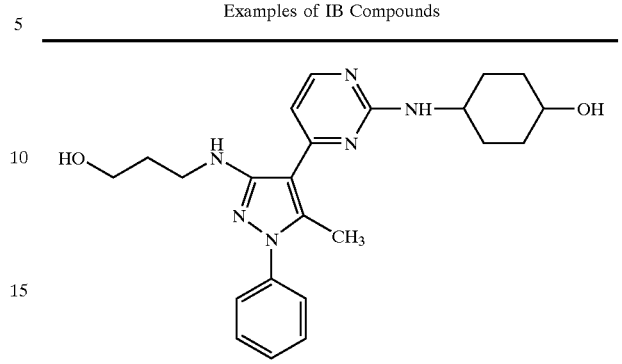

IB'-4

Other embodiments of this invention relate to compounds of formula I where G is —NH—R (formula IC), G is —NH—Ar (formula ID), G is —O—R (formula IE), G is —O—Ar (formula IF), G is —SO$_2$—R (formula IG), G is —SO$_2$—Ar (formula IH), G is —S(O)—R (formula IJ), and G is —S(O)—Ar (formula IK). Specific examples of these embodiments, wherein R$^3$ is phenyl, are shown below in Table 5.

TABLE 5

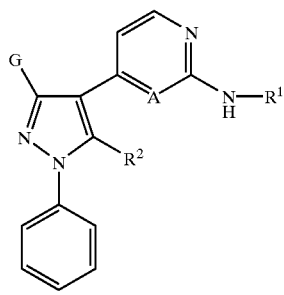

| No. | G | A | R$^1$ | R$^2$ |
|---|---|---|---|---|
| IC-1 | —NH-ethyl | CH | phenyl | CH$_3$ |
| IC-2 | —NH-propyl | N | phenyl | CH$_3$ |
| IC-3 | —NH-butyl | N | 3-CN-phenyl | CH$_3$ |
| IC-4 | —NH-isobutyl | N | phenyl | CH$_3$ |
| IC-5 | —NH—CH$_2$CH$_2$N(CH$_3$)$_2$ | N | 3-OCH$_3$-phenyl | CH$_3$ |
| ID-1 | —NH-phenyl | N | 3-OCH$_3$-phenyl | CH$_3$ |
| ID-2 | —NH-benzyl | N | phenyl | CH$_3$ |
| ID-3 | —NH-⟨piperidine⟩-N—CH$_3$ | N | phenyl | CH$_3$ |

TABLE 5-continued

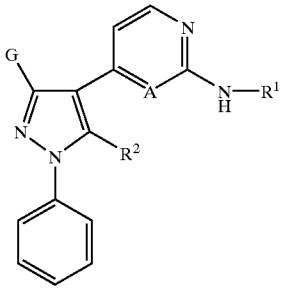

| No. | G | A | R¹ | R² |
|---|---|---|---|---|
| ID-4 | 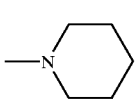 | N | 3,5-(OCH₃)₂-phenyl | CH₃ |
| ID-5 | 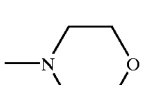 | N | 3,5-(OCH₃)₂-phenyl | CH₃ |
| ID-6 | 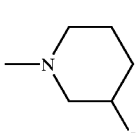 | N | 3,5-(OCH₃)₂-phenyl | CH₃ |
| ID-7 | 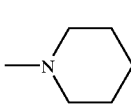 | N | 3,5-(OCH₃)₂-phenyl | CH₃ |
| ID-8 |  | N | 3,5-(OCH₃)₂-phenyl | CH₃ |
| ID-9 | 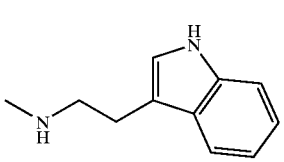 | N | phenyl | CH₃ |
| IE-1 | —O—CH₂CH₂N(CH₃)₂ | N | 4-CH₃-phenyl | CH₃ |
| IE-2 | —O-isobutyl | N | phenyl | CH₃ |
| IF-1 | —O-benzyl | N | 3,4-(OCH₃)₂-phenyl | CH₃ |
| IG-1 | —SO₂CH₃ | CH | phenyl | CH₃ |
| IG-2 | —SO₂-butyl | N | phenyl | CH₃ |
| IG-3 | —SO₂CH₃ | N | 3-OBn-phenyl | CH₃ |
| IH-1 | —SO₂-phenyl | N | 3-OCH₃-phenyl | CH₃ |
| IH-2 | SO₂-(4-CH₃-phenyl) | N | 3,4-(OCH₃)₂-phenyl | CH₃ |
| IH-2 | SO₂-(2-naphthyl) | N | 3,4-(OCH₃)₂-phenyl | CH₃ |
| IJ-1 | SO-butyl | N | phenyl | CH₃ |
| IK-1 | SO-phenyl | N | 3-OCH₃-phenyl | CH₃ |

The compounds of this invention may be prepared in general by methods known to those skilled in the art for analogous compounds, as illustrated by the general scheme below and the preparative examples that follow.

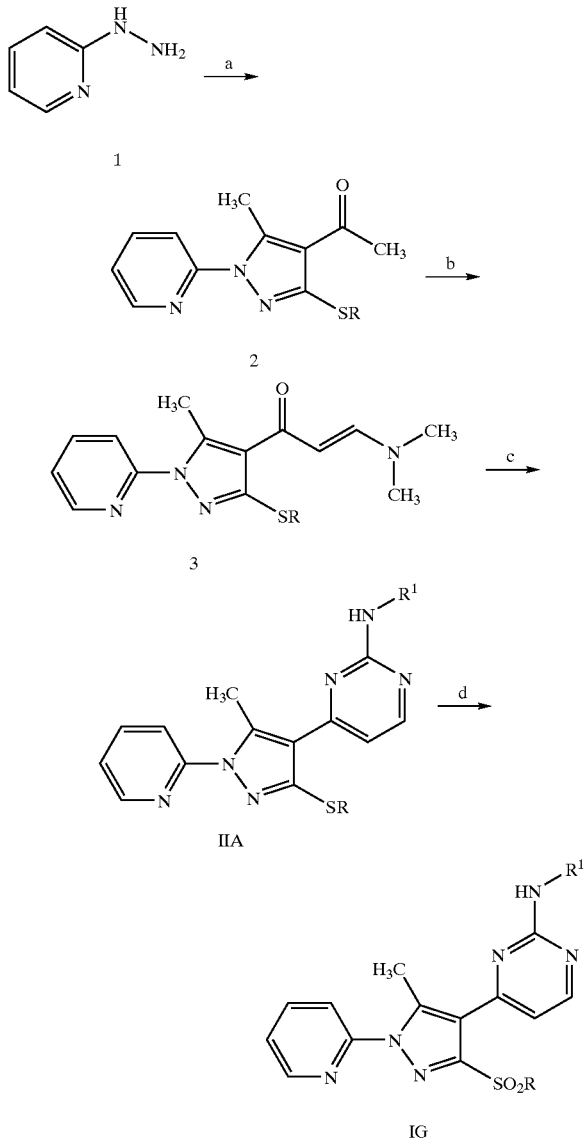

Reagents and conditions:
(a) (CH$_3$CO)$_2$C=C(SR)$_2$, 60° C.;
(b) DMF-DMA, toluene, reflux;
(c) R$^1$—NHC(=NH)NH$_2$, MeOH, reflux Scheme I above shows a general route to prepare the present compounds wherein R$^3$ is pyridyl. In step (a) pyridinylhydrazine is condensed with 3-(bis-alkylsulfanyl-methylene)-pentane-2,4-dione, for example using 3-(bis-methylsulfanyl-methylene)-pentane-2,4-dione to provide 2 (where R is methyl). Treatment of 2 with dimethylformamide-dimethylacetal (DMF-DMA) according to step (b) to provides the enamine 3. Compound 3 may be cyclized with various guanidine derivatives to provide compounds of formula IIA. Oxidation of a IIA compound with oxone provides the corresponding sulfonyl compound of formula IG. The sulfonyl group of IG, in turn, may be displaced by various amines to provide IC. Alternatively, the sulfonyl group or corresponding sulfoxide group may be displaced by —SAr, —SR, —OAr, or —OR to provide other compounds of this invention, using methods known to one of skill in the art.

The activity of a compound utilized in this invention as an inhibitor of JNK3, Lck, or Src, may be assayed in vitro, in vivo or in a cell line according to methods known in the art. In vitro assays include assays that determine inhibition of either the phosphorylation activity or ATPase activity of activated JNK3, Lck, or Src. Alternate in vitro assays quantitate the ability of the inhibitor to bind to JNK3, Lck, or Src. Inhibitor binding may be measured by radiolabelling the inhibitor prior to binding, isolating the inhibitor/JNK3, inhibitor/Lck, or inhibitor/Src complex and determining the amount of radiolabel bound. Alternatively, inhibitor binding may be determined by running a competition experiment where new inhibitors are incubated with JNK3, Lck, or Src bound to known radioligands. Detailed conditions for assaying a compound utilized in this invention as an inhibitor of JNK3, Lck, or Src kinase are set forth in the Examples below.

According to another embodiment, the invention provides a composition comprising a compound of this invention or a pharmaceutically acceptable derivative thereof and a pharmaceutically acceptable carrier, adjuvant, or vehicle. The amount of compound in the compositions of this invention is such that is effective to detectably inhibit a protein kinase, particularly JNK3, Lck, or Src in a biological sample or in a patient. Preferably the composition of this invention is formulated for administration to a patient in need of such composition. Most preferably, the composition of this invention is formulated for oral administration to a patient.

The term "patient", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The term "detectably inhibit", as used herein means a measurable change in JNK3, Lck, or Src activity between a sample comprising said composition and a JNK3, Lck, or Src kinase and an equivalent sample comprising JNK3, Lck, or Src kinase in the absence of said composition.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and $N^+(C_{1-4}\ alkyl)_4$ salts. This invention also envisions the quaternization of any basic nitrogen-containing groups of the compounds disclosed herein. Water or oil-soluble or dispersible products may be obtained by such quaternization.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

The amount of the compounds of the present invention that may be combined with the carrier materials to produce a composition in a single dosage form will vary depending upon the host treated, the particular mode of administration. Preferably, the compositions should be formulated so that a dosage of between 0.01–100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Depending upon the particular condition, or disease, to be treated or prevented, additional therapeutic agents, which are normally administered to treat or prevent that condition in a monotherapy, may also be present in the compositions of this invention. As used herein, additional therapeutic agents that are normally administered to treat or prevent a particular disease, or condition, are known as "appropriate for the disease, or condition, being treated".

For example, chemotherapeutic agents or other antiproliferative agents may be combined with the compounds of this invention to treat proliferative diseases and cancer. Examples of known chemotherapeutic agents include, but are not limited to, Gleevec™, adriamycin, dexamethasone, vincristine, cyclophosphamide, fluorouracil, topotecan, taxol, interferons, and platinum derivatives.

Other examples of agents the compounds of this invention may also be combined with include, without limitation, anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; agents for treating diabetes such as insulin, insulin analogues, alpha glucosidase inhibitors, biguanides, and insulin sensitizers; and agents for treating immunodeficiency disorders such as gamma globulin.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

According to another embodiment, the invention relates to a method of inhibiting JNK3, Lck, or Src kinase activity in a biological sample comprising the step of contacting said biological sample with a compound of this invention, or a composition comprising said compound.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of JNK3, Lck, or Src kinase activity in a biological sample is useful for a variety of purposes that are known to one of skill in the art. Examples of such purposes include, but are not limited to, blood transfusion, organtransplantation, biological specimen storage, and biological assays.

According to another embodiment, the invention provides a method for treating or lessening the severity of a JNK3-, Lck- or Src-mediated disease or condition in a patient comprising the step of administering to said patient a composition according to the present invention.

The term "JNK-mediated disease", as used herein means any disease or other deleterious condition in which JNK is known to play a role. Such conditions include, without limitation, inflammatory diseases, autoimmune diseases, destructive bone disorders, proliferative disorders, cancer, infectious diseases, neurodegenerative diseases, allergies, reperfusion/ischemia in stroke, heart attacks, angiogenic disorders, organ hypoxia, vascular hyperplasia, cardiac hypertrophy, thrombin-induced platelet aggregation, and conditions associated with prostaglandin endoperoxidase synthase-2.

Inflammatory diseases that may be treated or prevented by the compounds of this invention include, but are not limited to, acute pancreatitis, chronic pancreatitis, asthma, allergies, and adult respiratory distress syndrome.

Autoimmune diseases which may be treated or prevented by the compounds of this invention include, but are not limited to, glomerulonephritis, rheumatoid arthritis, systemic lupus erythematosus, scleroderma, chronic thyroiditis, Graves, disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, or graft vs. host disease.

Destructive bone disorders that may be treated or prevented by the compounds of this invention include, but are not limited to, osteoporosis, osteoarthritis and multiple myeloma-related bone disorder.

Proliferative diseases which may be treated or prevented by the compounds of this invention include, but are not limited to, acute myelogenous leukemia, chronic myelogenous leukemia, metastatic melanoma, Kaposi's sarcoma, multiple myeloma and HTLV-1 mediated tumorigenesis.

Angiogenic disorders that may be treated or prevented by the compounds of this invention include solid tumors, ocular neovasculization, infantile haemangiomas. Infectious diseases that may be treated or prevented by the compounds of this invention include, but are not limited to, sepsis, septic shock, and Shigellosis.

Viral diseases that may be treated or prevented by the compounds of this invention include, but are not limited to, acute hepatitis infection (including hepatitis A, hepatitis B and hepatitis C), HIV infection and CMV retinitis.

Neurodegenerative diseases that may be treated or prevented by the compounds of this invention include, but are not limited to, Alzheimer's disease, Parkinson's disease, amyotrophic lateral sclerosis (ALS), epilepsy, seizures, Huntington's disease, traumatic brain injury, ischemic and hemorrhaging stroke, cerebral ischemias or neurodegenerative disease, including apoptosis-driven neurodegenerative disease, caused by traumatic injury, acute hypoxia, ischemia or glutamate neurotoxicity.

"JNK-mediated diseases" also include ischemia/reperfusion in stroke, heart attacks, myocardial ischemia, organ hypoxia, vascular hyperplasia, cardiac hypertrophy, hepatic ischemia, liver disease, congestive heart failure, pathologic immune responses such as that caused by T cell activation and thrombin-induced platelet aggregation.

In addition, compounds of the instant invention may be capable of inhibiting the expression of inducible pro-inflammatory proteins. Therefore, other "JNK-mediated conditions" that may be treated by the compounds of this invention include edema, analgesia, fever and pain, such as neuromuscular pain, headache, cancer pain, dental pain and arthritis pain.

The compounds of this invention are also useful as inhibitors of Src-family kinases, especially Src and Lck. The term "Src-mediated or Lck-mediated disease", as used herein means any disease or other deleterious condition in which Src or Lck is known to play a role. Accordingly, these compounds are useful for treating diseases or conditions that are known to be affected by the activity of one or more Src-family kinases. Such diseases or conditions include hypercalcemia, restenosis, osteoporosis, osteoarthritis, symptomatic treatment of bone metastasis, rheumatoid arthritis, inflammatory bowel disease, multiple sclerosis, psoriasis, lupus, graft vs. host disease, T-cell mediated hypersensitivity disease, Hashimoto's thyroiditis, Guillain-Barre syndrome, chronic obtructive pulmonary disorder, contact dermatitis, cancer, Paget's disease, asthma, ischemic or reperfusion injury, allergic disease, atopic dermatitis, and allergic rhinitis. Diseases that are affected by Src activity, in particular, include hypercalcemia, osteoporosis, osteoarthritis, cancer, symptomatic treatment of bone metastasis, and Paget's disease. Diseases that are affected by Lck activity, in particular, include autoimmune diseases, allergies, rheumatoid arthritis, and leukemia.

A preferred embodiment relates to the method used to treat or prevent a JNK-mediated disease selected from inflammatory diseases, autoimmune diseases, destructive bone disorders, neurodegenerative diseases, allergies, reperfusion/ischemia in stroke, heart attacks, angiogenic disorders, organ hypoxia, vascular hyperplasia, cardiac hypertrophy, or thrombin-induced platelet aggregation.

Another preferred embodiment relates to the method used to treat or prevent a Src- or Lck-mediated disease selected from hypercalcemia, osteoperosis, osteoarthritis, or sympomatic treatment of bone metastasis.

In an alternate embodiment, the methods of this invention that utilize compositions that do not contain an additional therapeutic agent, comprise the additional step of separately administering to said patient an additional therapeutic agent. When these additional therapeutic agents are administered separately they may be administered to the patient prior to, sequentially with or following administration of the compositions of this invention.

The compounds of this invention or pharmaceutical compositions thereof may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Suitable coatings and the general preparation of coated implantable devices are described in U.S. Pat. Nos. 6,099,562; 5,886,026; and 5,304, 121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may be further covered by a suitable topcoat of fluorosilicone, polysaccarides, polyethylene glycol, phospholipids or combinations thereof to impart controlled release characteristics in the composition. Implantable devices coated with a compound of this invention are another embodiment of the present invention.

In order that the invention described herein may be more fully understood, the following examples are set forth. It should be understood that these examples are for illustrative purposes only and are not to be construed as limiting this invention in any manner.

SYNTHETIC EXAMPLES

Example 1

3-(Bis-methylsulfanyl-methylene)-pentane-2,4-dione

A DMF suspension of 2,4-pentanedione (1.0 equivalent), carbon disulfide (1.5 equivalents) and $K_2CO_3$ (1.5 equivalents) was stirred at 0° C. for 3 h. To the resulting suspension was added of iodomethane (3.0 equivalents) at 0° C., and the reaction mixture was allowed to warm to room temperature and stirred at that temperature overnight. To the reaction mixture was added ethyl acetate and brine, the organic phase was washed with brine twice and dried over magnesium sulfate, and filtered. The solvent was removed under reduced pressure and the product was crystallized to provide the title compound in 83% yield.

Example 2

1-(5-methyl-3-methylsulfanyl-1-pyridin-2-yl-1H-pyrazol-4-yl)-ethanone

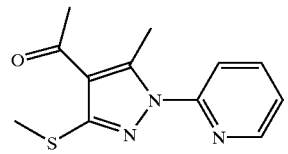

A mixture of pyridin-2-yl-hydrazine (1.0 equivalent) and 3-(bis-methylsulfanyl-methylene)-pentane-2,4-dione (1.0 equivalent) was stirred at 60° C. overnight. To the reaction mixture was added ethyl acetate and brine, the organic phase was washed by brine twice, dried over magensium sulfate, and filtered. The organic solvent was removed under reduced pressure to provide the title compound.

Example 3

3-Dimethylamino-1-(5-methyl-3-methylsulfanyl-1-pyridin-2-yl-1 H-pyrazol-4-yl)-propenone

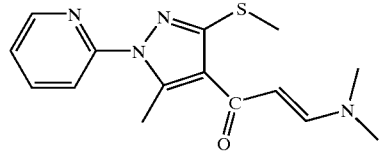

A toluene solution of 1-(5-methyl-3-methylsulfanyl-1-pyridin-2-yl-1H-pyrazol-4-yl)-ethanone (1.0 equivalent) and DMF-DMA (10.0 equivalent) was heated at reflux overnight. To the reaction mixture was added ethyl acetate and brine, the organic phase was washed with brine twice, dried over magnesium sulfate, and filtered. The solvent was removed under reduced pressure, and the crude product was purified by chromatograph to provide the title compound.

Example 4

N-(3-benzyloxy-phenyl)-guanidine

A 4 N HCl dioxane suspension of 3-benzyloxyaniline (1.0 equivalent) and cyanamide (1.0 equivalent) was stirred at 100° C. overnight. To the reaction mixture was added water and ether. The aqueous layer was washed with ether twice. The aqueous layer was adjusted to a pH greater 10 with 1M NaOH, and the desired guanidine was extracted to methylene chloride, precipitated and filtered. The filtration cake was N-(3-benzyloxy-phenyl)-guanidine (greater than 80% yield).

Example 5

(3-Benzyloxy-phenyl)-[4-(5-methyl-3-methylsulfanyl-1-pyridin-2-yl-1H-pyrazol-4-yl)-pyrimidin-2-yl]-amine (IIA-124)

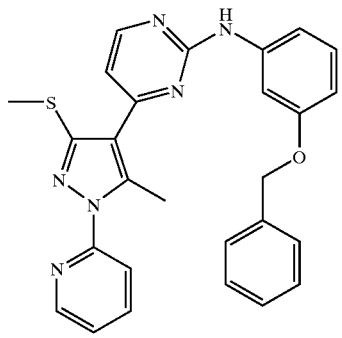

A methanol solution of 3-dimethylamino-1-(5-methyl-3-methylsulfanyl-1-pyridin-2-yl-1 H-pyrazol-4-yl)-propenone (1.0 equivalent) and N-(3-benzyloxy-phenyl)-guanidine (1.0 equivalent) was refluxed overnight. Analytical HPLC indicated the reaction was 40% complete. To the reaction mixture was added ethyl acetate and brine. The organic phase was washed with brine twice, dried over magnesium sulfate, and filtered. The product was precipitated and filtered to provide title compound in 40% yield.

Example 6

Phenyl-hydrazinecarbodithioic Acid Methyl Ester

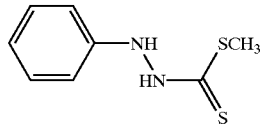

To a stirred solution of phenylhydrazine (30 mmol, 1 equiv) in dry acetonitrile (20 mL) was added trithiocarbonic acid dimethyl ester (30 mmol, 1 equiv) slowly at ice bath temperature. The mixture was stirred for 18 hours and diluted with diethylether (30 mL). The resulting white solid was filtered and was washed with ether and dried under nitrogen to afford title compound.

Example 7

1-(5-Methyl-3-methylsulfanyl-1-phenyl-1H-pyrazol-4-yl)-ethanone

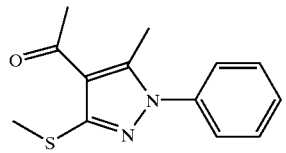

N-Phenyl-hydrazinecarbodithioic acid methyl ester (1.98 g, 10 mmol), 3-chloro-2,4-pentandione (1.35 g, 10 mmol), and diethyl isopropylamine(2.0 mL, 12 mmol) in acetonitrile (10 mL) was heated to 70 C for 10 hours. The mixture was diluted with ethyl acetate (30 mL) and water (30 mL). The organic layer was washed with water (30 mL). The aqueous layers were back extracted with ethyl acetate (30 mL, twice). The combined organic layers were dried with sodium sulfate and concentrated. The resulting solid was recrystalized with diethyl ether (30 mL) to afford pale yellow title compound.

Example 8

3-Dimethylamino-1-(5-methyl-3-methylsulfanyl-1-phenyl-1H-pyrazol-4-yl)-propenone

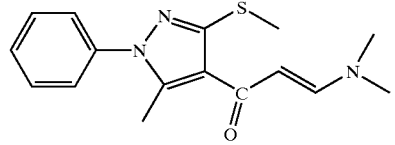

1-(5-Methyl-3-methylsulfanyl-1-phenyl-1H-pyrazol-4-yl)-ethanone (1.2 g, 5 mmol) and N,N-dimethylforamide dimethyl acetal (1.32 mL, 10 mmol) was diluted in acetonitrile (2 mL) and heated at 80 C for 36 hours. The mixture was diluted with diethyl ether (10 mL) and hexane (20 mL) and heated briefly. The yellow solid was collected and washed with diethyl ether (5 mL).

Example 9

[4-(5-Methyl-3-methylsulfanyl-1-phenyl-1H-pyrazol-4-yl)-pyrimidin-2-yl]-phenyl-amine (IIA-1)

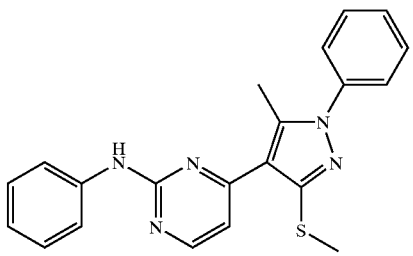

3-Dimethylamino-1-(5-methyl-3-methylsulfanyl-1-phenyl-1H-pyrazol-4-yl)-propenone (30 mg, 0.1 mmol) and N-phenylguanidine (15 mg, 1.1 equiv.) was slurried in acetonitrile (0.5 mL) and heated at 100 C for 24 hours. The mixture was diluted with methanol (2 mL) and heated briefly and cooled. The resulting solid was filtered and washed with methanol (1 mL). The solid was dried under reduced pressure to afford title compound.

Using the procedure described in Example 9 above except replacing N-phenylguanidine with the appropriately substituted N-phenylguanidine the following compounds were prepared. These compounds were purified by reverse phase HPLC and characterized by both NMR and LC/MS.

Example 10

(4-Fluoro-phenyl)-[4-(5-methyl-3-methylsulfanyl-1-phenyl-1H-pyrazol-4-yl)-pyrimidin-2-yl]-amine (IIA-9)

Example 11

(4-Chloro-phenyl)-[4-(5-methyl-3-methylsulfanyl-1-phenyl-1H-pyrazol-4-yl)-pyrimidin-2-yl]-amine (IIA-114)

Example 12

(3-Chloro-phenyl)-[4-(5-methyl-3-methylsulfanyl-1-phenyl-1H-pyrazol-4-yl)-pyrimidin-2-yl]-amine (IIA-115)

Example 13

(4-Nitro-phenyl)-[4-(5-methyl-3-methylsulfanyl-1-phenyl-1H-pyrazol-4-yl)-pyrimidin-2-yl]-amine (IIA-116)

Example 14

(3-Benzyloxy-phenyl)-[4-(5-methyl-3-methylsulfanyl-1-phenyl-1H-pyrazol-4-yl)-pyrimidin-2-yl]-amine (IIA-117)

Example 15

(4-Benzyloxy-phenyl)-[4-(5-methyl-3-methylsulfanyl-1-phenyl-1H-pyrazol-4-yl)-pyrimidin-2-yl]-amine (IIA-118)

Example 16

3-[4-(5-Methyl-3-methylsulfanyl-1-phenyl-1H-pyrazol-4-yl)-pyrimidin-2-ylamino]-phenol (IIA-119)

Src Inhibition Assays

The compounds were evaluated as inhibitors of human Src kinase using either a radioactivity-based assay or spectrophotometric assay.
Radioactivity-based Assay The compounds were assayed as inhibitors of full length recombinant human Src kinase (from Upstate Biotechnology, cat. no. 14–117) expressed and purified from baculo viral cells. Src kinase activity was monitored by following the incorporation of $^{33}P$ from ATP into the tyrosine of a random poly Glu-Tyr polymer substrate of composition, Glu:Tyr=4:1 (Sigma, cat. no. P-0275). The following were the final concentrations of the assay components: 0.025 M HEPES, pH 7.6, 10 mM $MgCl_2$, 2 mM DTT, 0.25 mg/ml BSA, 10 $\mu$M ATP (1–2 $\mu$Ci $^{33}P$-ATP per reaction), 5 mg/ml poly Glu-Tyr, and 1–2 units of recombinant human Src kinase. In a typical assay, all the reaction components with the exception of ATP were pre-mixed and aliquoted into assay plate wells. Inhibitors dissolved in DMSO were added to the wells to give a final DMSO concentration of 2.5%. The assay plate was incubated at 30° C. for 10 minutes before initiating the reaction with $^{33}P$-ATP. After 20 minutes of reaction, the reactions were quenched with 150 $\mu$l of 10% trichloroacetic acid (TCA) containing 20 mM $Na_3PO_4$. The quenched samples were then transferred to a 96-well filter plate (Whatman, UNI-Filter GF/F Glass Fiber Filter, cat no. 7700-3310) installed on a filter plate vacuum manifold. Filter plates were washed four times with 10% TCA containing 20 mM $Na_3PO_4$ and then 4 times with methanol. 200 $\mu$l of scintillation fluid was then added to each well. The plates were sealed and the amount of radioactivity associated with the filters was quantified on a TopCount scintillation counter. The radioactivity incorporated was plotted as a function of the inhibitor concentration. The data was fitted to a competitive inhibition kinetics model to get the $K_i$ for the compound.
Spectrophotometric Assay The ADP produced from ATP by the human recombinant src kinase-catalyzed phosphorylation of poly Glu-Tyr substrate was quanitified using a coupled enzyme assay (Fox et al (1998) *Protein Sci* 7, 2249). In this assay one molecule of NADH is oxidized to NAD for every molecule of ADP produced in the kinase reaction. The disappearance of NADH can be conveniently followed at 340 nm.

The following were the final concentrations of the assay components: 0.025 M HEPES, pH 7.6, 10 mM $MgCl_2$, 2 mM DTT, 0.25 mg/ml poly Glu-Tyr, and 25 nM of recombinant human Src kinase. Final concentrations of the components of the coupled enzyme system were 2.5 mM phosphoenolpyruvate, 200 $\mu$M NADH, 30 $\mu$g/ml pyruvate kinase and 10 $\mu$g/ml lactate dehydrogenase.

In a typical assay, all the reaction components with the exception of ATP were pre-mixed and aliquoted into assay plate wells. Inhibitors dissolved in DMSO were added to the wells to give a final DMSO concentration of 2.5%. The assay plate was incubated at 30° C. for 10 minutes before initiating the reaction with 100 $\mu$M ATP. The absorbance change at 340 nm with time, the rate of the reaction, was monitored on a molecular devices plate reader. The data of rate as a function of the inhibitor concentration was fitted to compettive inhibition kinetics model to get the $K_i$ for the compound.

Many of the present compounds tested in the Src inhibition assays provided a $K_i$ value below one micromolar.

Lck Inhibition Assays

The compounds were evaluated as inhibitors of human src kinase using either a radioactivity-based assay or spectrophotometric assay.
Radioactivity-based Assay The compounds were assayed as inhibitors of full length bovine thymus Lck kinase (from Upstate Biotechnology, cat. no. 14-106) expressed and purified from baculo viral cells. Lck kinase activity was monitored by following the incorporation of $^{33}P$ from ATP into the tyrosine of a random poly Glu-Tyr polymer substrate of composition, Glu:Tyr=4:1 (Sigma, cat. no. P-0275). The following were the final concentrations of the assay components: 0.025 M HEPES, pH 7.6, 10 mM $MgCl_2$, 2 mM DTT, 0.25 mg/ml BSA, 10 $\mu$M ATP (1–2 μCi $^{33}$P-ATP per reaction), 5 mg/ml poly Glu-Tyr, and 1–2 units of recombinant human Src kinase. In a typical assay, all the reaction components with the exception of ATP were pre-mixed and aliquoted into assay plate wells. Inhibitors dissolved in DMSO were added to the wells to give a final DMSO concentration of 2.5%. The assay plate was incubated at 30° C. for 10 minutes before initiating the reaction with $^{33}$P-ATP. After 20 minutes of reaction, the reactions were quenched with 150 μl of 10% trichloroacetic acid (TCA) containing 20 mM $Na_3PO_4$. The quenched samples were then transferred to a 96-well filter plate (Whatman, UNI-Filter GF/F Glass Fiber Filter, cat no. 7700-3310) installed on a filter plate vacuum manifold. Filter plates were washed four times with 10% TCA containing 20 mM $Na_3PO_4$ and then 4 times with methanol. 200 μl of scintillation fluid was then added to each well. The plates were sealed and the amount of radioactivity associated with the filters was quantified on a TopCount scintillation counter. The radioactivity incorporated was plotted as a function of the inhibitor concentration. The data was fitted to a competitive inhibition kinetics model to get the $K_i$ for the compound.

Spectrophotometric Assay

The ADP produced from ATP by the human recombinant Lck kinase-catalyzed phosphorylation of poly Glu-Tyr substrate was quanitified using a coupled enzyme assay (Fox et al (1998) *Protein Sci* 7, 2249). In this assay one molecule of NADH is oxidised to NAD for every molecule of ADP produced in the kinase reaction. The disappearance of NADH can be conveniently followed at 340 nm.

The following were the final concentrations of the assay components: 0.025 M HEPES, pH 7.6, 10 mM $MgCl_2$, 2 mM DTT, 5 mg/ml poly Glu-Tyr, and 50 nM of recombinant human Lck kinase. Final concentrations of the components of the coupled enzyme system were 2.5 mM phosphoenolpyruvate, 200 μM NADH, 30 μg/ml pyruvate kinase and 10 μg/ml lactate dehydrogenase.

In a typical assay, all the reaction components with the exception of ATP were pre-mixed and aliquoted into assay plate wells. Inhibitors dissolved in DMSO were added to the wells to give a final DMSO concentration of 2.5%. The assay plate was incubated at 30° C. for 10 minutes before initiating the reaction with 150 μM ATP. The absorbance change at 340 nm with time, the rate of the reaction, was monitored on a molecular devices plate reader. The data of rate as a function of the inhibitor concentration was fitted to competitive inhibition kinetics model to get the $K_i$ for the compound.

Many of the present compounds tested in the Lck inhibition assays provided an $K_i$ value below one micromolar.

JNK Inhibition Assays

Cloning, Expression and Purification of JNK3 Protein

A BLAST search of the EST database using the published JNK3α1 cDNA as a query identified an EST clone (#632588) that contained the entire coding sequence for human JNK3α1. Polymerase chain reactions (PCR) using pfu polymerase (Strategene) are used to introduce restriction sites into the cDNA for cloning into the pET-15B expression vector at the NcoI and BamHI sites. The protein is expressed in *E. coli*. Due to the poor solubility of the expressed full-length protein (Met 1-Gln 422), an N-terminally truncated protein starting at Ser residue at position 40 (Ser 40) is produced. This truncation corresponds to Ser 2 of JNK1 and JNK2 proteins, and is preceded by a methionine (initiation) and a glycine residue. The glycine residue is added in order to introduce an NcoI site for cloning into the expression vector. In addition, systematic C-terminal truncations are performed by PCR to identify a construct that give rise to diffraction-quality crystals. One such construct encodes amino acid residues Ser40-Glu402 of JNK3α1 and is preceded by Met and Gly residues.

The construct is prepared by PCR using deoxyoligonucleotides: 5' GCTCTAGAGCTCC ATGGGCAGCAAAAGCAAAGTTGACAA 3' (forward primer with initiation codon underlined) (SEQ ID NO:1) and 5' TAGCGGATCC TCATTCTGAATTCATTACTTCCTTGTA 3' (reverse primer with stop codon underlined) (SEQ ID NO:2) as primers and is confirmed by DNA sequencing. Control experiments indicated that the truncated JNK3 protein had an equivalent kinase activity towards myelin basic protein when activated with an upstream kinase MKK7 in vitro.

*E. coli* strain BL21 (DE3) (Novagen) is transformed with the JNK3 expression construct and grown at 30° C. in LB supplemented with 100 μg/ml carbenicillin in shaker flasks until the cells were in log phase ($OD_{600}$~0.8). Isopropylthio-β-D-galactosidase (IPTG) is added to a final concentration of 0.8 mM and the cells are harvested 2 hours later by centrifugation.

*E. coli* cell paste containing JNK3 is resuspended in 10 volumes/g lysis buffer (50 mM HEPES, pH 7.2, containing 10% glycerol (v/v), 100 mM NaCl, 2 mM DTT, 0.1 mM PMSF, 2 μg/ml Pepstatin, 1 μg/ml each of E-64 and Leupeptin). Cells are lysed on ice using a microfluidizer and centrifuged at 100,000×g for 30 minutes at 4° C. The 100,000×g supernatant is diluted 1:5 with Buffer A (20 mM HEPES, pH 7.0, 10% glycerol (v/v), 2 mM DTT) and purified by SP-Sepharose (Pharmacia) cation-exchange chromatography (column dimensions: 2.6×20 cm) at 4° C. The resin is washed with 5 column volumes of Buffer A, followed by 5 column volumes of Buffer A containing 50 mM NaCl. Bound JNK3 is eluted with a 7.5 column volume linear gradient of 50–300 mM NaCl. JNK3 eluted between 150–200 mM NaCl.

Example 9

Activation of JNK3

5 mg of JNK3 is diluted to 0.5 mg/ml in 50 mM HEPES buffer, pH 7.5, containing 100 mM NaCl, 5 mM DTT, 20 mM $MgCl_2$ and 1 mM ATP. GST-MKK7(DD) is added at a molar ratio of 1:2.5 GST-MKK7:JNK3. After incubation for 30 minutes at 25° C., the reaction mixture is concentrated 5-fold by ultrafiltration in a Centriprep-30 (Amicon, Beverly, Mass.), diluted to 10 ml and an additional 1 mM ATP added. This procedure is repeated three times to remove ADP and replenish ATP. The final addition of ATP is 5 mM and the mixture incubated overnight at 4° C.

The activated JNK3/GST-MKK7(DD) reaction mixture is exchanged into 50 mM HEPES buffer, pH 7.5, containing 5 mM DTT and 5% glycerol (w/v) by dialysis or ultrafiltration. The reaction mixture is adjusted to 1.1 M potassium phosphate, pH 7.5, and purified by hydrophobic interaction chromatography (at 25° C.) using a Rainin Hydropore column. GST-MKK7 and unactivated JNK3 do not bind under these conditions such that when a 1.1 to 0.05 M potassium phosphate gradient is developed over 60 minutes at a flow rate of 1 ml/minute, doubly phosphorylated JNK3 is separated from singly phosphorylated JNK. Activated JNK3 (i.e. doubly phosphorylated JNK3) is stored at −70° C. at 0.25–1 mg/ml.

Example 10

JNK Inhibition Assay

Compounds are assayed for the inhibition of JNK3 by a spectrophotometric coupled-enzyme assay. In this assay, a fixed concentration of activated JNK3 (10 nM) is incubated with various concentrations of a potential inhibitor dissolved in DMSO for 10 minutes at 30° C. in a buffer containing 0.1 M HEPES buffer, pH 7.5, containing 10 mM $MgCl_2$, 2.5 mM phosphoenolpyruvate, 200 $\mu$M NADH, 150 $\mu$g/mL pyruvate kinase, 50 $\mu$g/mL lactate dehydrogenase, and 200 $\mu$M EGF receptor peptide. The EGF receptor peptide has the sequence KRELVEPLTPSGEAPNQALLR(SEQ ID NO:3), and is a phosphoryl acceptor in the JNK3-catalyzed kinase reaction. The reaction is initiated by the addition of 10 $\mu$M ATP and the assay plate is inserted into the spectrophotometer's assay plate compartment that is maintained at 30° C. The decrease of absorbance at 340 nm is monitored as a function of time and the percent inhibition is determined.

Many of the present compounds tested in the JNK3 inhibition assays were found to inhibit JNK3.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

---

I claim:
1. A compound of formula I:

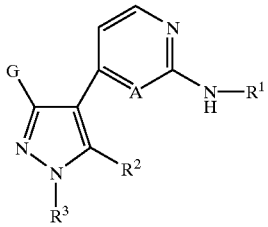

or a pharmaceutically acceptable salt thereof, wherein:
G is —XR or —XAr;
  each X is independently selected from a $C_{1-4}$ alkylidene chain, wherein one or two non-adjacent methylene units of X are independently replaced by —S—, —SO—, —SO$_2$—, —O—, or —NH—;
A is N;
each R is independently selected from hydrogen or an optionally substituted $C_{1-8}$ aliphatic group;

Ar is an optionally substituted ring selected from phenyl, pyridyl, imidazolyl, thienyl, thiazolyl, [1,3]dioxanyl, piperidinyl, morpholinyl, pyrrolyl, pyrrolidinyl, furanyl, tetrahydrofuranyl, pyranyl, imidazolyl, benzimidazolyl, pyrrolyl, piperazinyl, thiomorpholinyl, naphthyl, oxazolyl, triazinyl, tetrazolyl, dithiolanyl, dioxalanyl, benzofuranyl, benzothienyl, or indolyl;

$R^1$ is $T_{(n)}$-R or $T_{(n)}$ attached to an optionally susbtituted ring selected from phenyl, cyclohexyl, pyridyl, naphthyl, quinolinyl, isoquinolinyl, or indanyl;
n is zero or one;
T is selected from —C(O)—, —CO$_2$—, —C(O)C(O)—, —C(O)CH$_2$C(O)—, —CONR—, —S(O)$_2$—, or —S(O)$_2$NR—;
$R^2$ is selected from hydrogen, Ar, or a $C_{1-8}$ aliphatic group optionally substituted with 1–3 groups independently selected from oxo, OR, SR, SO$_2$R, C(O)R, CO$_2$R, CN, N(R)$_2$, =N—OR, =NN(R)$_2$, =NNHC(O)R, =NNHCO$_2$R, =NNHSO$_2$R, Ar, NRC(O)N(R)$_2$, NRC(O)R, NRCO$_2$R, C(O)N(R)$_2$, SO$_2$N(R)$_2$, or NRSO$_2$N(R)$_2$; and $R^3$ is selected from R or an optionally substituted ring selected from cyclohexyl, cyclopentyl, phenyl, pyridyl, pyrimidinyl, or pyridazinyl.
2. The compound according to claim 1, wherein:
R is a $C_{1-4}$ aliphatic group optionally substituted with halo, CN, oxo, N(R$^o$)$_2$, OH, OR$^o$, CO$_2$R$^o$, C(O)R$^o$, C(O)N(R$^o$)$_2$, NR$^o$CO$_2$R$^o$, SR$^o$, NR$^o$SO$_2$R$^o$, SO$_2$R$^o$, NR$^o$C(O)R$^o$, OC(O)R$^o$, or NR$^o$C(O)N(R$^o$)$_2$, wherein each R$^o$ group is independently selected from hydrogen or $C_{1-4}$ aliphatic;

Ar is an optionally substituted ring selected from phenyl, pyridyl, imidazolyl, thienyl, thiazolyl, [1,3]dioxanyl, piperidinyl, morpholinyl, pyrrolyl, pyrrolidinyl, furanyl, tetrahydrofuranyl, pyranyl, imidazolyl, benzimidazolyl, pyrrolyl, piperazinyl, thiomorpholinyl, naphthyl, oxazolyl, triazinyl, tetrazolyl, dithiolanyl, dioxalanyl, benzofuranyl, benzothienyl, or indolyl; and $R^3$ is selected from an optionally substituted cyclohexyl, cyclopentyl, phenyl, pyridyl, pyrimidinyl, or pyridazinyl ring.
3. The compound according to claim 1, wherein:
$R^2$ is selected from R, CH$_2$N(R)$_2$, or CH$_2$Ar, wherein:
  each R is independently selected from hydrogen or optionally substituted $C_{1-4}$ aliphatic, and
  Ar is an optionally substituted ring selected from phenyl, pyridyl, [1,3]dioxanyl, piperidinyl, morpholinyl pyranyl, or piperazinyl.
4. The compound according to claim 1, wherein:
when n is zero, then $R^1$ is $T_{(n)}$ attached to an attached to an optionally subsbtituted rin selected from phenyl, cyclohehyl, pyridyl, naphthyl, quinolinyl, isoquinolinyl, or indanyl.
5. The compound according to claim 4, wherein:
$R^1$ is phenyl, cyclohexyl, pyridyl, naphthyl, quinolinyl, isoquinolinyl, or indanyl, wherein:
  $R^1$ is optionally substituted with 1–3 groups independently selected from R$^o$, halogen, NO$_2$, CN, OR$^o$, SR$^o$, N(R$^o$)$_2$, CO$_2$R$^o$, C(O)R$^o$, CON(R$^o$)$_2$, phenyl, SO$_2$R$^o$, or NR$^o$C(O)R$^o$, wherein each R$^o$ is independently selected from hydrogen or an optionally substituted $C_{1-4}$ aliphatic.
6. The compound according to claim 5, wherein $R^1$ is optionally sutstituted with 1–3 groups independently selected from methyl, ethyl, oxo, CF$_3$, Ome, C(O)Me, C(O)phenyl, CH=CH, CO$_2$H, C(O)NH$_2$, SMe, CO$_2$Me, fluoro, SO$_2$Me, NO$_2$, OC, chloro, N(Me)$_2$, NHC(O)Me, NH$_2$, cyanophenyl, CO$_2$Et, CH$_2$OH, CH$_2$OMe, 3-CH$_2$CO$_2$H-phenyl, or 3-CH$_2$CH$_2$CO$_2$H-phenyl.
7. The compound according to claim 4, wherein:
$R^2$ is selected from R, CH$_2$N(R)$_2$, or CH$_2$Ar, wherein:
  each R is independently selected from hydrogen or optionally substituted $C_{1-4}$ aliphatic, and
  Ar is an optionally substituted ring selected from phenyl, cyclohexyl, or pyridyl.

8. A compound selected from:

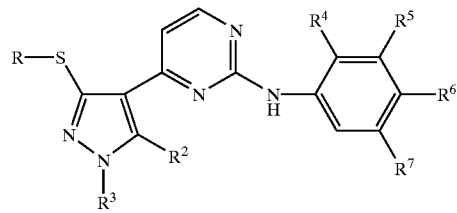

| No. | S-R | $R^2$ | $R^3$ | $R^4$ | $R^5$ | $R^6$ | $R^7$ |
|---|---|---|---|---|---|---|---|
| IIA-1 | $SCH_3$ | Me | Ph | H | H | H | H |
| IIA-2 | $SCH_3$ | Me | Ph | H | H | OMe | H |
| IIA-3 | $SCH_3$ | Me | Ph | H | OMe | OMe | H |
| IIA-4 | $SCH_3$ | Me | Ph | Me | H | H | H |
| IIA-5 | $SCH_3$ | Me | Ph | Me | H | $CONH_2$ | H |
| IIA-6 | $SCH_3$ | Me | Ph | Me | H | CN | H |
| IIA-7 | $SCH_3$ | Me | Ph | H | CN | H | H |
| IIA-8 | $SCH_3$ | Me | Ph | Me | F | H | H |
| IIA-9 | $SCH_3$ | Me | Ph | Me | H | F | H |
| IIA-10 | $SCH_3$ | Me | Ph | $CF_3$ | H | H | H |
| IIA-11 | $SCH_3$ | Et | Ph | H | CN | H | H |
| IIA-12 | $SCH_3$ | Et | Ph | H | $CO_2H$ | H | H |
| IIA-13 | $SCH_3$ | Me | Ph | H | F | H | H |
| IIA-14 | $SCH_3$ | Me | Ph | H | H | F | H |
| IIA-15 | $SCH_3$ | Me | Ph | H | H | COMe | H |
| IIA-16 | $SCH_3$ | Me | Ph | H | H | COPh | H |
| IIA-17 | $SCH_3$ | Me | Ph | H | H | $CONH_2$ | H |
| IIA-18 | $SCH_3$ | Me | Ph | H | OMe | H | OMe |
| IIA-19 | $SCH_3$ | Me | Ph | H | F | H | H |
| IIA-20 | $SCH_3$ | Me | Ph | H | H | CN | H |
| IIA-21 | $SCH_3$ | Me | Ph | H | H | COMe | H |
| IIA-22 | $SCH_3$ | Me | Ph | H | CH=CH | H | H |
| IIA-23 | $SCH_3$ | Me | Ph | H | SMe | H | H |
| IIA-24 | $SCH_3$ | Me | Ph | H | Me | CN | H |
| IIA-25 | $SCH_3$ | Me | Ph | H | COMe | H | H |
| IIA-26 | $SCH_3$ | Et | Ph | H | H | H | H |
| IIA-27 | $SCH_3$ | Me | Ph | OMe | H | H | H |
| IIA-28 | $SCH_3$ | Me | Ph | H | H | F | H |
| IIA-29 | $SCH_3$ | Me | Ph | H | $CO_2H$ | H | H |
| IIA-30 | $SCH_3$ | Me | Ph | H | H | Ph | H |
| IIA-31 | $SCH_3$ | Me | Ph | H | Me | H | Me |
| IIA-32 | $SCH_3$ | Me | Ph | H | H | SMe | H |
| IIA-33 | $SCH_3$ | Me | Ph | H | H | OMe | H |
| IIA-34 | $SCH_3$ | Me | Ph | H | OMe | H | H |
| IIA-35 | $SCH_3$ | Me | Ph | OMe | H | H | CN |
| IIA-36 | $SCH_3$ | Me | Ph | H | $CO_2Me$ | H | H |
| IIA-37 | $SCH_3$ | Me | Ph | F | H | H | CN |
| IIA-38 | $SCH_3$ | Me | Ph | H | H | H | H |
| IIA-39 | $SCH_3$ | Me | Ph | H | H | $CO_2H$ | H |
| IIA-40 | $SCH_3$ | Me | Ph | Me | H | CN | H |
| IIA-41 | $SCH_3$ | Me | Ph | F | H | F | H |
| IIA-42 | $SCH_3$ | Me | Ph | Me | H | $CONH_2$ | H |
| IIA-43 | $SCH_3$ | Me | Ph | Me | Cl | H | H |
| IIA-44 | $SCH_3$ | Me | Ph | F | H | H | H |
| IIA-45 | $SCH_3$ | Me | Ph | Me | H | OMe | H |
| IIA-46 | $SCH_3$ | Me | Ph | OMe | H | H | H |
| IIA-47 | $SCH_3$ | Me | Ph | H | H | $SO_2Me$ | H |
| IIA-48 | $SCH_3$ | Me | Ph | H | H | $CO_2Me$ | H |
| IIA-49 | $SCH_3$ | Me | Ph | $NO_2$ | H | H | H |
| IIA-50 | $SCH_3$ | Me | Ph | H | CN | H | H |
| IIA-51 | $SCH_3$ | Me | Ph | H | H | CN | H |
| IIA-52 | $SCH_3$ | Me | Ph | CHCH | H | H | H |
| IIA-53 | $SCH_3$ | Me | Ph | Me | F | H | H |
| IIA-54 | $SCH_3$ | Me | Ph | Cl | H | H | OMe |
| IIA-55 | $SCH_3$ | Me | Ph | H | Me | OMe | H |
| IIA-56 | $SCH_3$ | Me | Ph | Me | H | F | H |
| IIA-57 | $SCH_3$ | Me | Ph | SMe | H | H | H |
| IIA-58 | $SCH_3$ | Me | Ph | OMe | H | H | OMe |
| IIA-59 | $SCH_2CH_3$ | Me | Ph | H | H | H | H |
| IIA-60 | $SCH_2CH_3$ | Me | Ph | H | CN | H | H |
| IIA-61 | $SCH_2CH_3$ | Me | Ph | H | H | CN | H |
| IIA-62 | $SCH_2CH_3$ | Me | Ph | H | F | H | H |
| IIA-63 | $SCH_2CH_3$ | Me | Ph | H | H | F | H |
| IIA-64 | $SCH_2CH_3$ | Me | Ph | H | Me | CN | H |

-continued

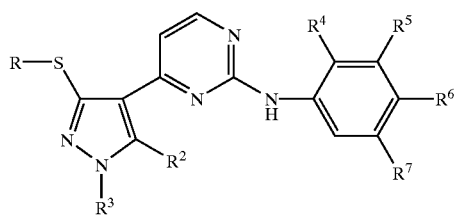

| No. | S-R | R² | R³ | R⁴ | R⁵ | R⁶ | R⁷ |
|---|---|---|---|---|---|---|---|
| IIA-65 | SCH₂CH₃ | Me | Ph | H | F | CN | H |
| IIA-66 | SCH₂CH₃ | Me | Ph | H | H | SMe | H |
| IIA-67 | SCH(CH₃)₂ | Me | Ph | H | H | H | H |
| IIA-68 | SCH₂CH(CH₃)₂ | Me | Ph | H | H | H | H |
| IIA-69 | S-propyl | Me | Ph | H | H | H | H |
| IIA-70 | S-butyl | Me | Ph | H | H | H | H |
| IIA-71 | S-pentyl | Me | Ph | H | H | H | H |
| IIA-72 | S-hexyl | Me | Ph | H | H | H | H |
| IIA-73 | S-heptyl | Me | Ph | H | H | H | H |
| IIA-74 | S-octyl | Me | Ph | H | H | H | H |
| IIA-75 | SCH₂CN | Me | Ph | H | H | H | H |
| IIA-76 | SCH₂CH₂OCH₃ | Me | Ph | H | H | H | H |
| IIA-77 | SCH₂CH₂CF₃ | Me | Ph | H | H | H | H |
| IIA-78 | SCH₂(cyclopropyl) | Me | Ph | H | H | H | H |
| IIA-79 | SCH₂C(=O)CH₃ | Me | Ph | H | H | H | H |
| IIA-80 | SCH₂CH₂N(CH₃)₂ | Me | Ph | H | H | H | H |
| IIA-81 | SCH₂CH₂NHCOCH₃ | Me | Ph | H | H | H | H |
| IIA-82 | SCH₂CH₂NHCO₂CH₃ | Me | Ph | H | H | H | H |
| IIA-83 | SCH₂CH₂OC(=O)CH₃ | Me | Ph | H | H | H | H |
| IIA-84 | SCH₂CH(NH₂)CO₂Et | Me | Ph | H | H | H | H |
| IIA-85 | SCH₂C≡CCH₃ | Me | Ph | H | H | H | H |
| IIA-86 | S-propyl | Me | Ph | H | H | COMe | H |
| IIA-87 | S-propyl | Me | Ph | H | CN | H | H |
| IIA-88 | S-propyl | Me | Ph | H | H | CN | H |
| IIA-89 | S-propyl | Me | Ph | H | F | H | H |
| IIA-90 | S-propyl | Me | Ph | H | H | F | H |
| IIA-91 | S-propyl | Me | Ph | H | CN | F | H |
| IIA-92 | S-propyl | Me | Ph | H | H | SMe | H |
| IIA-93 | SCH₃ | Me | Ph | H | H | NMe₂ | H |
| IIA-94 | SCH₃ | Me | Ph | H | NO₂ | H | H |
| IIA-95 | SCH₃ | Me | Ph | H | NHAc | H | H |
| IIA-96 | SCH₃ | Me | Ph | H | NH₂ | H | H |
| IIA-97 | SCH₃ | Me | Ph | H | Me | H | H |
| IIA-98 | SCH₃ | Me | Ph | H | H | Me | H |
| IIA-99 | S-butyl | Me | Ph | H | F | CN | H |
| IIA-100 | S-butyl | Me | Ph | H | F | H | H |
| IIA-101 | S-butyl | Me | Ph | H | H | CN | H |
| IIA-102 | S-butyl | Me | Ph | H | Me | H | H |
| IIA-103 | S-butyl | Me | Ph | H | CN | H | H |
| IIA-105 | S-pentyl | Me | Ph | H | F | CN | H |
| IIA-106 | S-pentyl | Me | Ph | H | CN | H | H |
| IIA-107 | SCH₂CH(CH₃)₂ | Me | Ph | H | F | CN | H |
| IIA-108 | SCH₂CH(CH₃)₂ | Me | Ph | H | CN | H | H |
| IIA-109 | SCH₂CH(CH₃)₂ | Me | Ph | | | | |

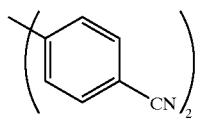

bis-N,N'-4-cyanophenol

-continued

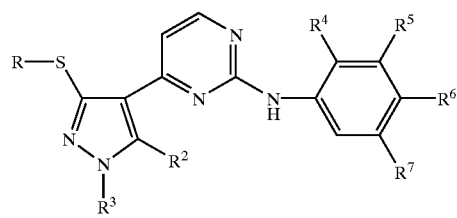

| No. | S-R | R² | R³ | R⁴ | R⁵ | R⁶ | R⁷ |
|---|---|---|---|---|---|---|---|
| IIA-110 | SCH₂C≡CCH₃ | Me | Ph | H | F | CN | H |
| IIA-111 | SCH₂C≡CCH₃ | Me | Ph | H | CN | H | H |
| IIA-112 | SCH₂C≡CCH₃ | Me | Ph | H | H | H | H |
| IIA-113 | SCH₃ | Me | Ph | H | CO₂Et | H | H |
| IIA-114 | SCH₃ | Me | Ph | H | H | Cl | H |
| IIA-115 | SCH₃ | Me | Ph | H | Cl | H | H |
| IIA-116 | SCH₃ | Me | Ph | H | H | NO₂ | H |
| IIA-117 | SCH₃ | Me | Ph | H | OCH₂Ph | H | H |
| IIA-118 | SCH₃ | Me | Ph | H | H | OCH₂Ph | H |
| IIA-119 | SCH₃ | Me | Ph | H | OH | H | H |
| IIA-120 | SCH₃ | Me | Ph | \multicolumn{4}{c}{3-(CH₂CH₂CO₂H)phenyl} | | | |
| IIA-121 | SCH₃ | Me | Ph | \multicolumn{4}{c}{3-(CH₂CO₂H)phenyl} | | | |
| IIA-122 | SCH₃ | Me | Ph | \multicolumn{4}{c}{3-[CH₂CH₂C(O)NH-CH(iPr)CO₂tBu]phenyl} | | | |
| IIA-123 | SCH₃ | Me | 2-Pyr | H | H | H | H |
| IIA-124 | SCH₃ | Me | 2-Pyr | H | OCH₂Ph | H | H |
| IIA-125 | SCH₃ | Me | 3-Pyr | H | OCH₂Ph | H | H |
| IIA-126 | SCH₃ | Me | 4-Pyr | H | OCH₂Ph | H | H |
| IIA-127 | SCH₃ | Me | Ph | H | Cl | H | H |
| IIA-128 | SCH₃ | Me | 2-Pyr | H | H | OCH₂Ph | H |
| IIA-129 | CH₂CH₂SCH₃ | Me | Ph | H | OCH₂Ph | H | H |
| IIA-130 | CH₂CH₂SCH₃ | Me | Ph | H | OPh | H | H |
| IIA-131 | CH₂CH₂SCH₃ | Me | Ph | H | Cl | H | H |
| IIA-132 | CH₂CH₂SCH₃ | Me | Ph | H | OMe | H | H |
| IIA-133 | CH₂CH₂SCH₃ | Me | Ph | H | CO₂CH₃ | H | H |
| IIA-134 | SCH₃ | Me | Ph | H | OH | H | H. |

9. A compound selected from:
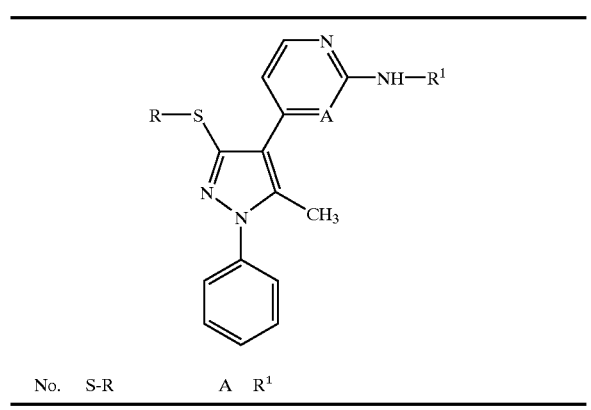
| No. | S-R | A | R¹ |
|---|---|---|---|
| IIA-137 | SCH₃ | N | 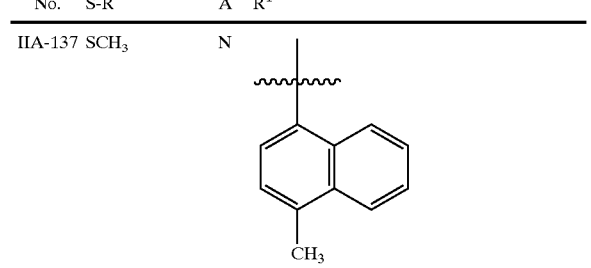 |
| IIA-138 | SCH₃ | N | 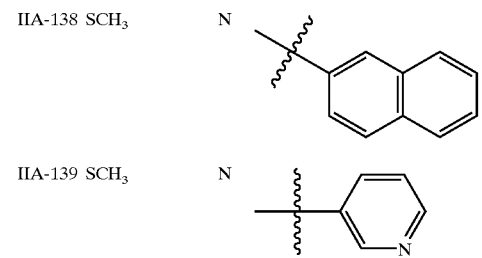 |
| IIA-139 | SCH₃ | N | 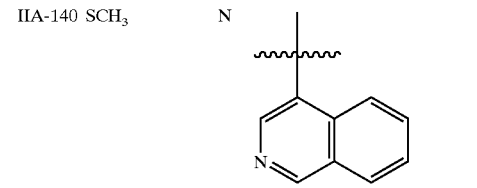 |
| IIA-140 | SCH₃ | N | 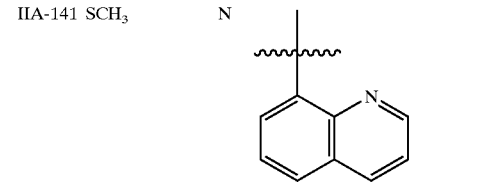 |
| IIA-141 | SCH₃ | N | 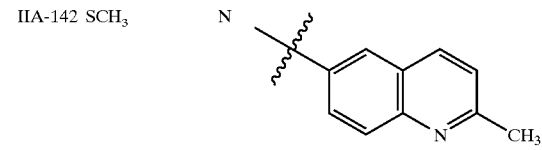 |
| IIA-142 | SCH₃ | N | 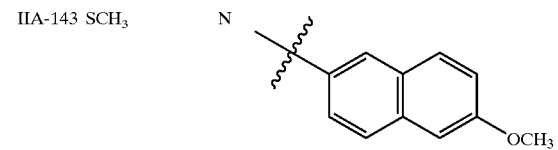 |
| IIA-143 | SCH₃ | N | |
-continued
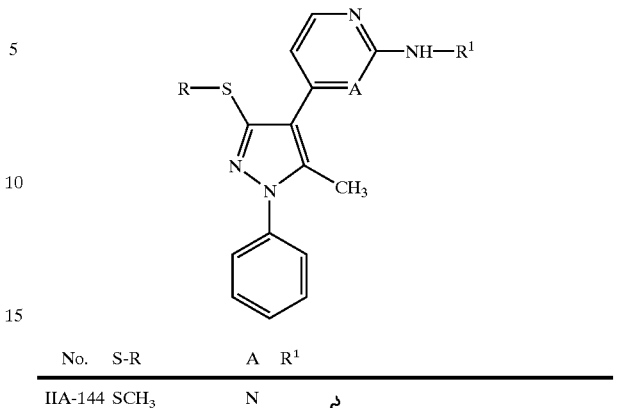
| No. | S-R | A | R¹ |
|---|---|---|---|
| IIA-144 | SCH₃ | N | 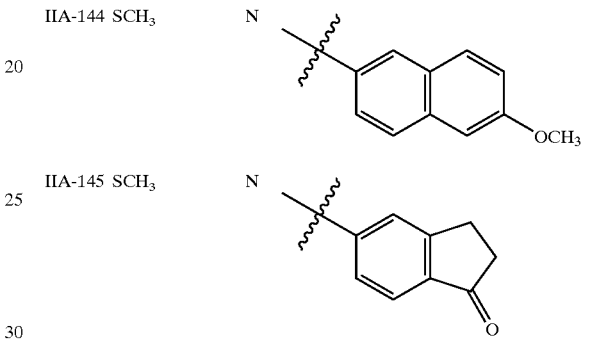 |
| IIA-145 | SCH₃ | N | 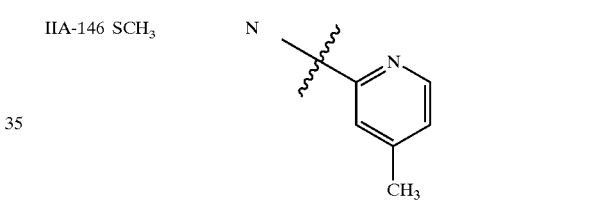 |
| IIA-146 | SCH₃ | N | 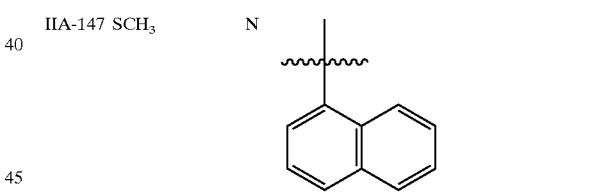 |
| IIA-147 | SCH₃ | N | 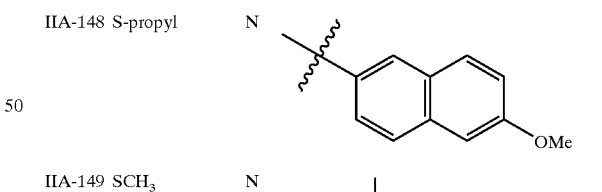 |
| IIA-148 | S-propyl | N | 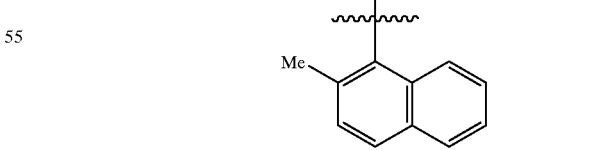 |
| IIA-149 | SCH₃ | N | 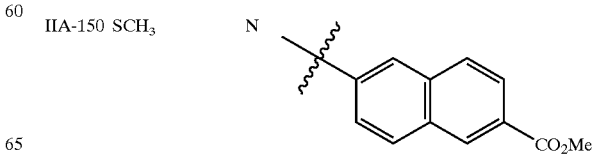 |
| IIA-150 | SCH₃ | N | |

-continued
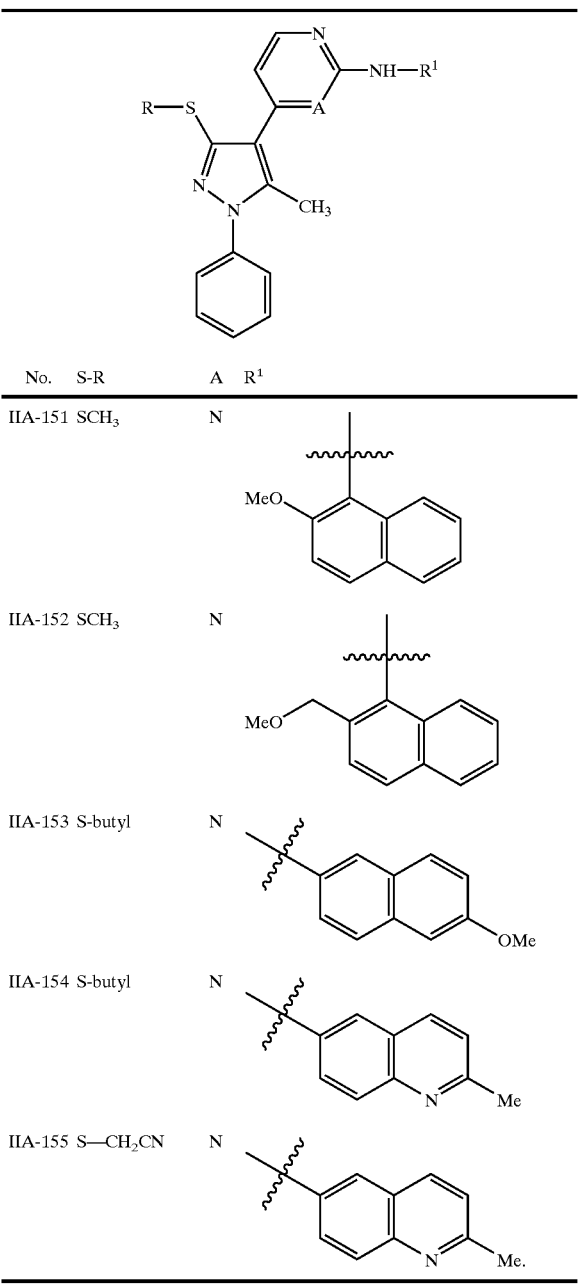
| No. | S-R | A | R¹ |
|---|---|---|---|
| IIA-151 | SCH₃ | N | (1-position, 2-OMe naphthyl) |
| IIA-152 | SCH₃ | N | (1-position, 2-CH₂OMe naphthyl) |
| IIA-153 | S-butyl | N | (6-position, 2-OMe naphthyl) |
| IIA-154 | S-butyl | N | (6-position, 2-Me quinolinyl) |
| IIA-155 | S—CH₂CN | N | (6-position, 2-Me quinolinyl) |
10. A compound selected from:
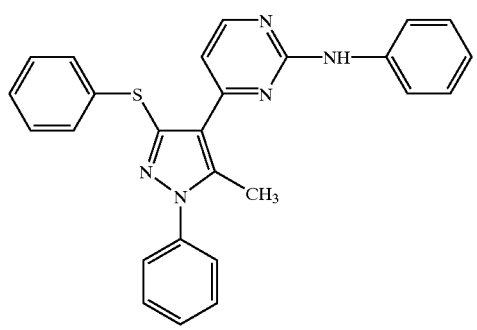
IB-1
-continued
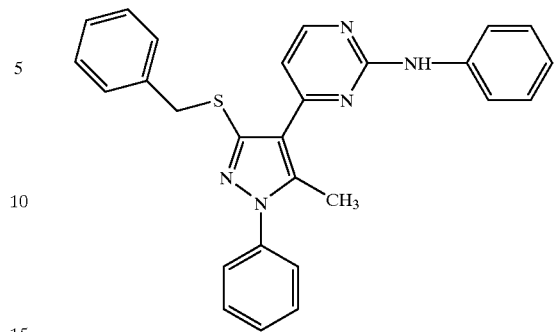
IB-2
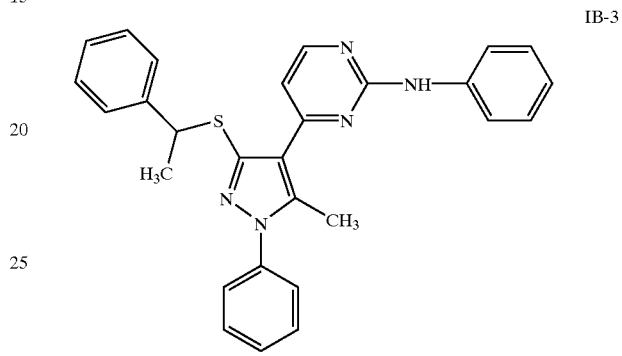
IB-3
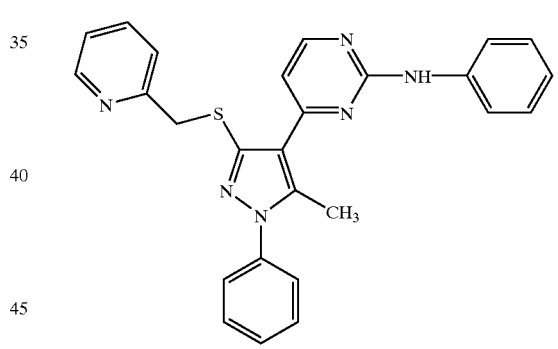
IB-4
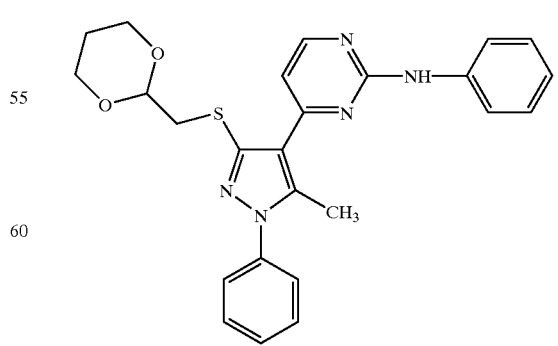
IB-5

IB-6
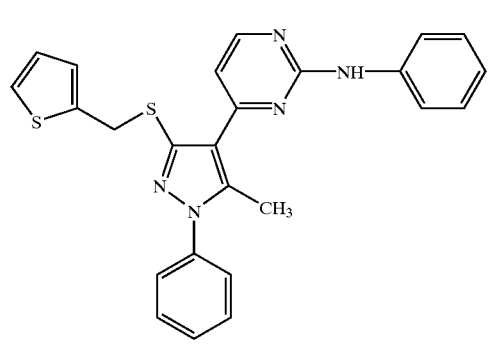
IB-7
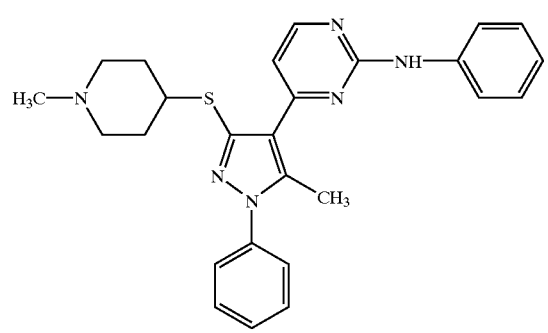
IB-8
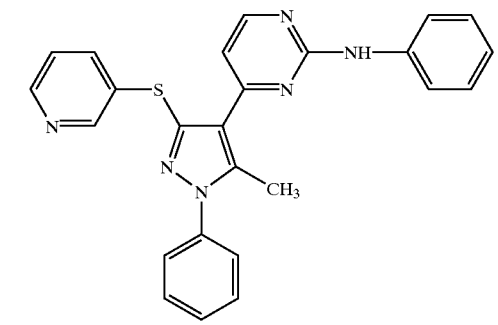
IB-9
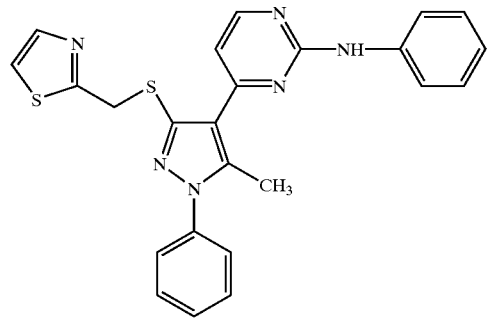
IB-10
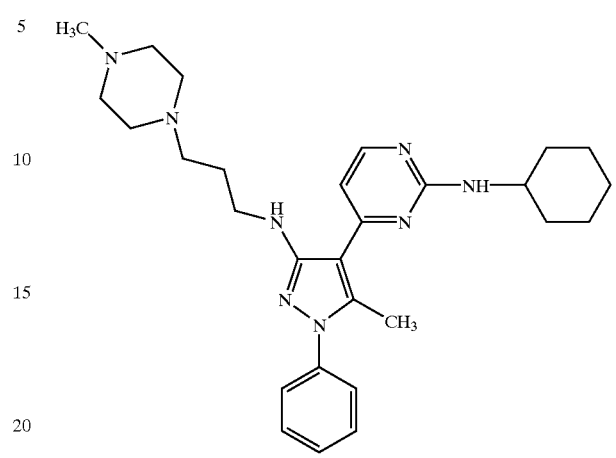
IB-11
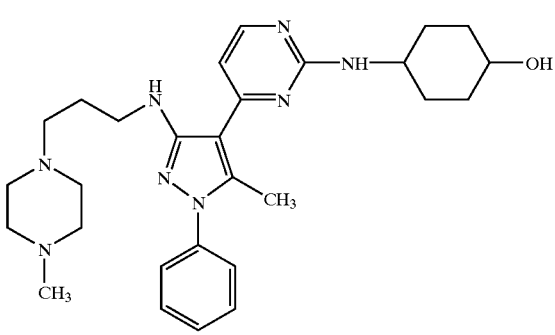
IB-12
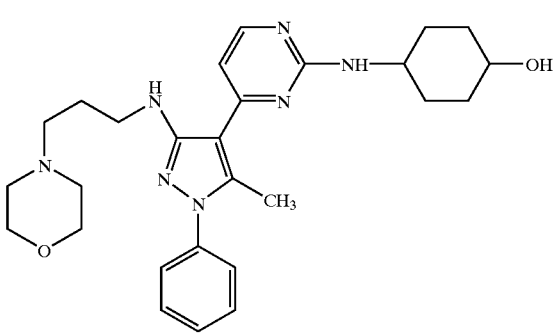

-continued
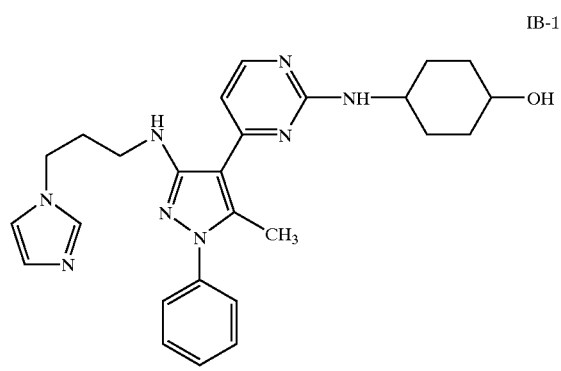
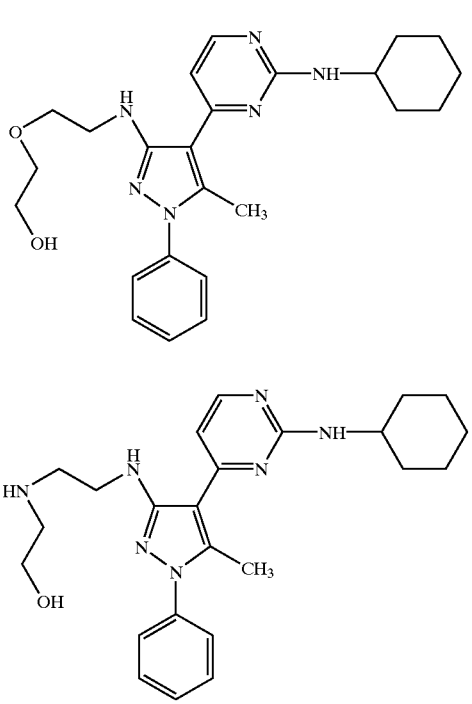
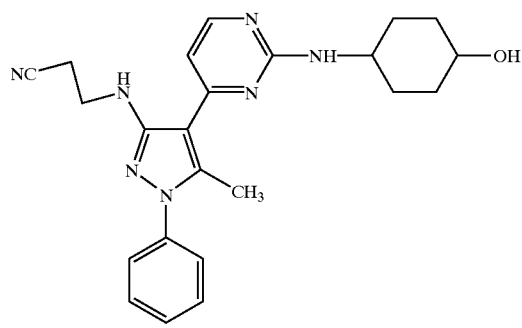
or
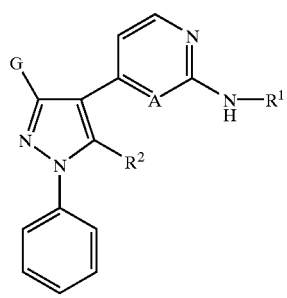
11. A compound selected from:
TABLE 5
| No. | G | A | R$^1$ | R$^2$ |
|-----|---|---|-------|-------|
| IC-2 | —NH-propyl | N | phenyl | CH$_3$ |
| IC-3 | —NH-butyl | N | 3-CN-phenyl | CH$_3$ |
| IC-4 | —NH-isobutyl | N | phenyl | CH$_3$ |

TABLE 5-continued

| No. | G | A | R¹ | R² |
|---|---|---|---|---|
| IC-5 | —NH—CH$_2$CH$_2$N(CH$_3$)$_2$ | N | 3-OCH$_3$-phenyl | CH$_3$ |
| ID-1 | —NH-phenyl | N | 3-OCH$_3$-phenyl | CH$_3$ |
| ID-2 | —NH-benzyl | N | phenyl | CH$_3$ |
| ID-3 | —NH-(1-methylpiperidin-4-yl) | N | phenyl | CH$_3$ |
| ID-4 | piperidin-1-yl | N | 3,5-(OCH$_3$)$_2$-phenyl | CH$_3$ |
| ID-5 | morpholin-4-yl | N | 3,5-(OCH$_3$)$_2$-phenyl | CH$_3$ |
| ID-6 | 3-hydroxypiperidin-1-yl | N | 3,5-(OCH$_3$)$_2$-phenyl | CH$_3$ |
| ID-7 | 4-hydroxypiperidin-1-yl | N | 3,5-(OCH$_3$)$_2$-phenyl | CH$_3$ |
| ID-8 | —NH—CH$_2$CH$_2$OH | N | 3,5-(OCH$_3$)$_2$-phenyl | CH$_3$ |
| ID-9 | —NH—CH$_2$CH$_2$-(1H-indol-3-yl) | N | phenyl | CH$_3$ |
| IE-1 | —O—CH$_2$CH$_2$N(CH$_3$)$_2$ | N | 4-CH$_3$-phenyl | CH$_3$ |
| IE-2 | —O-isobutyl | N | phenyl | CH$_3$ |
| IF-1 | —O-benzyl | N | 3,4-(OCH$_3$)$_2$-phenyl | CH$_3$ |
| IG-2 | —SO$_2$-butyl | N | phenyl | CH$_3$ |
| IG-3 | —SO$_2$CH$_3$ | N | 3-OBn-phenyl | CH$_3$ |
| IH-1 | —SO$_2$-phenyl | N | 3-OCH$_3$-phenyl | CH$_3$ |
| IH-2 | SO$_2$-(4-CH$_3$-phenyl) | N | 3,4-(OCH$_3$)$_2$-phenyl | CH$_3$ |
| IH-2 | SO$_2$-(2-naphthyl) | N | 3,4-(OCH$_3$)$_2$-phenyl | CH$_3$ |
| IJ-1 | SO-butyl | N | phenyl | CH$_3$ |
| IK-1 | SO-phenyl | N | 3-OCH$_3$-phenyl | CH$_3$. |

12. A composition comprising a compound according to any one of claim 8, 9, 10, or 11, and a pharmaceutically acceptable carrier, adjuvant, or vehicle.

13. A method of inhibiting JNK3, Lck, or Src kinase activity in a biological sample comprising the step of contacting said biological sample with:

a) a compound according to any one of claim 8, 9, 10, or or 11; or
b) a composition according to claim 12.

14. A method of treating or lessening the severity of a JNK3-, Lck-, or Src-mediated disease or condition in a patient comprising the step of administering to said patient a composition according to claim 12.

15. A method of treating or lessening the severity of an inflammatory disease, autoimmune disease, destructive bone disorder, proliferative disorder, infectious disease, neurodegenerative disease, allergy, reperfusion/ischemia in stroke, heart attack, angiogenic disorder, organ hypoxia, vascular hyperplasia, cardiac hypertrophy, thrombin-induced platelet aggregation or a condition associated with proinflammatory cytokines comprising the step of administering to said patient a composition according to claim 12.

16. The method according to claim 15, wherein said method is used to treat an inflammatory disease selected from acute pancreatitis, chronic pancreatitis, asthma, allergies, or adult respiratory distress syndrome.

17. The method according to claim 15, wherein said method is used to treat an autoimmune disease selected from glomerulonephritis, rheumatoid arthritis, systemic lupus erythematosus, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, or graft vs. host disease.

18. The method according to claim 15, wherein said method is used to treat a destructive bone disorders selected from osteoarthritis, osteoporosis or multiple myeloma-related bone disorder.

19. The method according to claim 15, wherein said method is used to treat a proliferative disease selected from acute myelogenous leukemia, chronic myelogenous leukemia, metastatic melanoma, Kaposi's sarcoma, or multiple myeloma.

20. The method according to claim 15, wherein said method is used to treat neurodegenerative disease selected from Alzheimer's disease, Parkinson's disease, amyotrophic lateral sclerosis, Huntington's disease, cerebral ischemia or neurodegenerative disease caused by traumatic injury, glutamate neurotoxicity or hypoxia.

21. The method according to claim 15, wherein said method is used to treat ischemia/reperfusion in stroke or myocardial ischemia, renal ischemia, heart attacks, organ hypoxia or thrombin-induced platelet aggregation.

22. The method according to claim 15, wherein said method is used to treat a condition associated with T-cell activation or pathologic immune responses.

23. The method according to claim 15, wherein said method is used to treat an angiogenic disorder selected from solid tumors, ocular neovasculization, or infantile haemangiomas.

24. The method according to claim 14, wherein said disease is selected from hypercalcemia, restenosis, hypercalcemia, osteoporosis, osteoarthritis, symptomatic treatment of bone metastasis, rheumatoid arthritis, inflammatory bowel disease, multiple sclerosis, psoriasis, lupus, graft vs. host disease, T-cell mediated hypersensitivity disease, Hashimoto's thyroiditis, Guillain-Barre syndrome, chronic obtructive pulmonary disorder, contact dermatitis, cancer, Paget's disease, asthma, ischemic or reperfusion injury, allergic disease, atopic dermatitis, or allergic rhinitis.

25. The method according to claim 24, wherein said disease is selected from hypercalcemia, osteoperosis, osteoarthritis, or sympomatic treatment of bone metastasis.

26. The method according to claim 14, wherein said disease is selected from autoimmune diseases, allergies, rheumatoid arthritis, and leukemia.

* * * * *

SEQUENCE LISTING

```
<160> NUMBER OF SEQ ID NOS: 3

<210> SEQ ID NO 1
<211> LENGTH: 39
<212> TYPE: PRT
<213> ORGANISM: Homo sapiens

<400> SEQUENCE: 1

Gly Cys Thr Cys Thr Ala Gly Ala Gly Cys Thr Cys Ala Thr Gly
1               5                   10                  15

Gly Gly Cys Ala Gly Cys Ala Ala Ala Gly Cys Ala Ala Ala Gly
                20                  25                  30

Thr Thr Gly Ala Cys Ala Ala
            35

<210> SEQ ID NO 2
<211> LENGTH: 37
<212> TYPE: PRT
<213> ORGANISM: Homo sapiens

<400> SEQUENCE: 2

Thr Ala Gly Cys Gly Gly Ala Thr Cys Cys Thr Cys Ala Thr Thr Cys
1               5                   10                  15

Thr Gly Ala Ala Thr Thr Cys Ala Thr Thr Ala Cys Thr Thr Cys Cys
                20                  25                  30

Thr Thr Gly Thr Ala
            35

<210> SEQ ID NO 3
<211> LENGTH: 21
<212> TYPE: PRT
<213> ORGANISM: Homo sapiens

<400> SEQUENCE: 3

Lys Arg Glu Leu Val Glu Pro Leu Thr Pro Ser Gly Glu Ala Pro Asn
1               5                   10                  15

Gln Ala Leu Leu Arg
            20
```